(12) United States Patent
Nogami

(10) Patent No.: US 8,268,333 B2
(45) Date of Patent: Sep. 18, 2012

(54) ORALLY ADMINISTERED AGENT AND AN ORALLY ADMINISTERED AGENT/SUPPORTING SUBSTRATE COMPLEX

(75) Inventor: Eiji Nogami, Saitama (JP)

(73) Assignee: Lintec Corporation, Tokyo (JP)

( * ) Notice: Subject to any disclaimer, the term of this patent is extended or adjusted under 35 U.S.C. 154(b) by 278 days.

(21) Appl. No.: 12/591,700

(22) Filed: Nov. 30, 2009

(65) Prior Publication Data

US 2010/0112015 A1     May 6, 2010

Related U.S. Application Data

(63) Continuation-in-part of application No. 10/690,811, filed on Oct. 23, 2003, now abandoned, which is a continuation of application No. PCT/JP02/03920, filed on Apr. 19, 2002, which is a continuation-in-part of application No. 11/540,952, filed on Oct. 2, 2006, now abandoned, which is a continuation of application No. PCT/JP2005/004569, filed on Mar. 15, 2005.

(30) Foreign Application Priority Data

| Apr. 24, 2001 | (JP) | 2001-125804 |
|---|---|---|
| Mar. 31, 2004 | (JP) | 2004-106854 |

(51) Int. Cl.
| A61K 9/00 | (2006.01) |
|---|---|
| A61K 9/20 | (2006.01) |
| A61K 9/28 | (2006.01) |
| A61K 9/30 | (2006.01) |
| A61K 9/32 | (2006.01) |
| A61K 47/00 | (2006.01) |
| A61K 47/30 | (2006.01) |
| A61K 47/32 | (2006.01) |

(52) U.S. Cl. ........ 424/400; 424/464; 424/474; 424/475; 424/482; 514/772; 514/772.3; 514/772.6

(58) Field of Classification Search .................. 424/400, 424/464, 474, 475, 485; 514/772, 772.3, 514/772.6

See application file for complete search history.

(56) References Cited

U.S. PATENT DOCUMENTS

| 2,513,852 A | 7/1950 | Donofrio |
|---|---|---|
| 4,075,104 A | 2/1978 | Ringel |

(Continued)

FOREIGN PATENT DOCUMENTS

CA     2 339 836     3/2000

(Continued)

OTHER PUBLICATIONS

European Search Report mailed Jan. 11, 2011 issued in corresponding EP patent application No. 02 724 622.2.

(Continued)

Primary Examiner — Abigail Fisher
(74) Attorney, Agent, or Firm — Posz Law Group, PLC

(57) ABSTRACT

With an object of providing an orally administered agent (in particular a film-shaped orally administered agent) with which the ease and safety of taking the agent are improved, to attain this object, in an orally administered agent 1b having one drug-containing layer 11 and two water-swellable gel-forming layers 12, the water-swellable gel-forming layers 12 are provided, either directly or via intermediate layers, on the both faces of the drug-containing layer 11.

15 Claims, 9 Drawing Sheets

U.S. PATENT DOCUMENTS

| | | | |
|---|---|---|---|
| 4,765,983 A | | 8/1988 | Takayanagi et al. |
| 4,849,246 A | | 7/1989 | Schmidt |
| 4,855,142 A | | 8/1989 | Fankhauser et al. |
| 5,137,729 A | | 8/1992 | Kuroya et al. |
| 5,456,745 A | | 10/1995 | Roreger et al. |
| 5,582,838 A | | 12/1996 | Rork et al. |
| 5,617,920 A | * | 4/1997 | Dovan et al. ................. 166/295 |
| 5,626,866 A | | 5/1997 | Ebert et al. |
| 5,626,874 A | * | 5/1997 | Conte et al. ................. 424/464 |
| 5,629,003 A | | 5/1997 | Horstmann et al. |
| 5,766,620 A | | 6/1998 | Heiber et al. |
| 5,824,338 A | | 10/1998 | Jacobs et al. |
| 5,824,339 A | | 10/1998 | Shimizu et al. |
| 5,914,118 A | | 6/1999 | Yamamura et al. |
| 5,993,846 A | | 11/1999 | Friedman et al. |
| 6,020,706 A | | 2/2000 | Iwashita et al. |
| 6,120,802 A | | 9/2000 | Breitenbach et al. |
| 6,136,344 A | | 10/2000 | Depui et al. |
| 6,153,222 A | | 11/2000 | Becher |
| 6,242,004 B1 | | 6/2001 | Rault |
| 6,641,839 B1 | | 11/2003 | Geoghegan et al. |
| 6,709,678 B2 | | 3/2004 | Gruber |
| 6,797,283 B1 | | 9/2004 | Edgren et al. |
| 7,115,280 B2 | | 10/2006 | Hanna et al. |
| 2002/0068088 A1 | | 6/2002 | Gruber |
| 2004/0137040 A1 | | 7/2004 | Nogami |
| 2005/0089548 A1 | | 4/2005 | Virgalitto et al. |
| 2007/0141152 A1 | | 6/2007 | Nogami |
| 2007/0141153 A1 | | 6/2007 | Nogami |
| 2007/0202171 A1 | | 8/2007 | Nogami |
| 2008/0254102 A9 | | 10/2008 | Nogami |

FOREIGN PATENT DOCUMENTS

| | | |
|---|---|---|
| CA | 2 262 595 | 10/2005 |
| CN | 1312710 A | 9/2001 |
| CN | 1356102 A | 7/2002 |
| CN | 1462194 A | 12/2003 |
| EP | 0 448 231 | 4/1995 |
| EP | 1391212 A1 | 2/2004 |
| JP | A-61-068415 | 4/1986 |
| JP | A-62-207208 | 9/1987 |
| JP | A-63-501794 | 7/1988 |
| JP | A-01-272520 | 10/1989 |
| JP | A-03-106813 | 5/1991 |
| JP | A-04-211608 | 8/1992 |
| JP | A-05-500514 | 2/1993 |
| JP | A-05-124954 | 5/1993 |
| JP | A-05-220203 | 8/1993 |
| JP | A-05-310561 | 11/1993 |
| JP | A-07-100186 | 4/1995 |
| JP | A-09-132522 | 5/1997 |
| JP | A-09-276374 | 10/1997 |
| JP | A-10-024091 | 1/1998 |
| JP | A-10-500973 | 1/1998 |
| JP | A-10-029932 | 2/1998 |
| JP | A-11-116469 | 4/1999 |
| JP | A-2000-024089 | 1/2000 |
| JP | A-2000-119128 | 4/2000 |
| JP | A-2001-028074 | 1/2001 |
| JP | A-2001-288074 | 10/2001 |
| JP | A-2004-196784 | 7/2004 |
| JP | A-2005-080838 | 3/2005 |
| JP | B2-4267926 | 5/2009 |
| WO | WO 87/02241 | 4/1987 |
| WO | WO 91/04017 | 4/1991 |
| WO | WO 95/33452 | 12/1995 |
| WO | WO 98/06385 | 2/1998 |
| WO | WO 00/35448 | 6/2000 |
| WO | WO 01/19901 | 3/2001 |
| WO | WO 02/087622 | 11/2002 |
| WO | WO 2005/087205 | 9/2005 |
| WO | WO 2005/097080 | 10/2005 |
| WO | WO 2005/097198 | 10/2005 |

OTHER PUBLICATIONS

Office Action mailed Oct. 21, 2008 issued in corresponding JP patent application No. 2002-584964.
Office Action mailed Jun. 30, 2008 issued in corresponding JP patent application No. 2002-584964.
U.S. Appl. No. 10/592,953, filed Sep. 15, 2006, Nogami.
U.S. Appl. No. 11/540,954, filed Oct. 2, 2006, Nogami.
Office Action dated Sep. 12, 2008 in related U.S. Appl. No. 10/592,953.
Final Office Action dated Apr. 20, 2009 in related U.S. Appl. No. 10/592,953.
Advisory Action dated Jul. 27, 2009 in related U.S. Appl. No. 10/592,953.
Office Action dated Aug. 4, 2008 in related U.S. Appl. No. 11/540,954.
Final Office Action dated Jan. 9, 2009 in related U.S. Appl. No. 11/540,954.
Advisory Action dated Apr. 15, 2009 in related U.S. Appl. No. 11/540,954.
Office Action dated Jun. 23, 2009 in related U.S. Appl. No. 11/540,954.
The Society of Polymer Science, Japan, edited by Kobunshi Jiten Henshu Iinkai, Kobunshi Jiten, Kabushiki Kaisha Asakura Shoten, Nov. 20, 1976, p. 532.
Fuseau et al., "Effect of Encapsulation on Absorption on Absorption of Sumatriptan Tablets: Data from Healthy Volunteers and Patients During a Migraine," *Clinical Therapeutics*, vol. 23, No. 2, 2001, pp. 242-245.
USB Online Product Guide, "PVP-K-90," http://www.usbweb.com/category.asp?special=&cat=117&id=20612#, accessed on Jul. 23, 2008.
Office Action issued from Chinese Patent Office on Jul. 24, 2009 in corresponding Chinese patent application No. 2005800163741 of the related U.S. Appl. No. 11/540,952.
International Search Report dated Jul. 30, 2002 in PCT Application No. PCT/JP02/03920 (and English translation).
International Search Report dated Jul. 12, 2005 in PCT Application No. PCT/JP2005/004567 (and English translation).
International Search Report dated Jul. 12, 2005 in PCT Application No. PCT/JP2005/004568 (and English translation).
International Search Report dated Jul. 12, 2005 in PCT Application No. PCT/JP2005/004569 (and English translation).
Office Action dated May 12, 2009 issued in corresponding Canadian patent application No. 2,445,347.
Final Office Action dated Jan. 7, 2010 in related U.S. Appl. No. 11/540,954.
Office Action dated Sep. 28, 2009 issued in corresponding AU application No. 2008201149.
European Search Report dated Apr. 26, 2011 issued in corresponding EP application No. 05 720 824.1.

* cited by examiner (a)

(b)

(c)

ORALLY ADMINISTERED AGENT AND AN ORALLY ADMINISTERED AGENT/SUPPORTING SUBSTRATE COMPLEX

CROSS REFERENCE TO RELATED APPLICATIONS

This application is a continuation-in-part application of U.S. patent application Ser. No. 10/690,811 filed on Oct. 23, 2003 and entitled AN ORALLY ADMINISTERED AGENT AND AN ORALLY ADMINISTERED AGENT/SUPPORTING SUBSTRATE COMPLEX, which in turn is a continuation application of PCT Application No. PCT/JP02/03920 filed on Apr. 19, 2002, and which claims priority from Japanese Application No. 2001-125804 filed on Apr. 24, 2001, the contents of each being incorporated herein by reference. This application is also a continuation-in-part application of U.S. patent application Ser. No. 11/540,952 filed on Oct. 2, 2006 and entitled ORALLY ADMINISTERED PHARMACEUTICAL COMPOSITION, which in turn is a continuation application of PCT Application No. PCT/JP05/04569 filed on Mar. 15, 2005, and which claims priority from Japanese Application No. 2004-106854 filed on Mar. 31, 2004, the contents of each being incorporated herein by reference.

TECHNICAL FIELD

The present invention relates to an orally administered agent and an orally administered agent/supporting substrate complex.

BACKGROUND ART

There are cases in which compliance of taking an orally administered agent drops by an unpleasant feeling due to the drug being bitter, astringent or the like, nausea or vomiting due to taking the drug, or refusal to take the drug. Various forms of orally administered agents have thus been developed.

Typically used forms of orally administered agents are solid preparations such as tablets and capsules. However, these solid preparations are difficult to swallow as it is, and must generally be taken with a large amount of water; even when taken with a large amount of water, there are cases in which swallowing is still difficult. There are thus cases in which compliance of taking the drug drops. Moreover, there are cases in which a solid preparation mistakenly gets stuck in the trachea, and cases in which a solid preparation sticks to the esophagus and hence an esophageal ulcer forms in this place.

In particular, it may not be possible for elderly people and infants to swallow a solid preparation, and hence a drop in compliance of taking the drug is often seen. Moreover, in the case of bedridden patients, after putting the solid preparation into the patient's mouth, giving water slowly, and then waiting a while, it is necessary for the care provider to feel around with his/her own fingers inside the patient's mouth to check that the solid preparation is not still there, and thus the work of checking whether or not the preparation has been taken is very burdensome.

To improve upon the difficulty of swallowing a solid preparation, and thus increase the ease and safety of taking the solid preparation, one can envisage making the form into a semi-solid form such as a jelly. However, a semi-solid preparation such as a jelly is difficult to realize due to the problems that a lot of moisture is contained, and hence the stability of the drug drops (particularly in the case of a readily hydrolyzable drug), sterile handling is difficult during manufacture and storage, and packaging is expensive.

On the other hand, by processing an orally administered agent into a film-shaped preparation (sheet-shaped preparation), the moisture content in the preparation can be kept down, and hence the stability of the drug can be improved (particularly in the case of a readily hydrolyzable drug), handling becomes easy, and the packaging cost can be reduced.

Regarding such film-shaped preparations, film-shaped preparations for which an object is to make disintegration or dissolution occur rapidly in the mouth (Japanese Patent Application Laid-open No. H7-100186, Japanese Patent Application Laid-open No. H5-220203, Japanese Patent Application Laid-open No. H11-116469), and film-shaped preparations for which an object is to make handling of a minute amount of a drug easy (Japanese Patent Application Laid-open No. H5-124954) are known.

DISCLOSURE OF THE INVENTION

However, these film-shaped preparations are not improved sufficiently with regard to ease and safety of taking the preparation, strength of the film-shaped preparation, and so on.

For example, in the case of the above-mentioned film-shaped preparations for which an object is to make disintegration or dissolution occur rapidly in the mouth, the drug rapidly spreads through the mouth before the preparation is swallowed, and hence there is a drop in compliance of taking the drug due to the taste (e.g. bitterness, astringency) or smell of the drug. In the case of using a drug that is bitter or the like, processing such as making into a microcapsule is thus necessary.

Moreover, in the case of the above-mentioned film-shaped preparations for which an object is to make disintegration or dissolution occur rapidly in the mouth, it is not possible to visually check that a bedridden patient has taken the preparation, and hence as with a conventional solid preparation, this must be done by feeling around inside the patient's mouth, and thus the work of checking that the preparation has been taken is very burdensome.

Moreover, in the case of most of the above-mentioned film-shaped preparations, the film-shaped preparation is manufactured by mixing the drug and a component necessary for the film formation (e.g. a film-forming agent) together, and hence if the content of the drug in the film-shaped preparation increases, then the content of the component necessary for the film formation drops correspondingly, and hence the strength of the film-shaped preparation drops.

Moreover, in the case of the film-shaped preparations for which an object is to make handling of a minute amount of a drug easy, there are limitations on the types of drugs that can be contained in the preparation.

It is thus a first object of the present invention to provide an orally administered agent (in particular a film-shaped orally administered agent) according to which the ease and safety of taking the agent are improved.

Moreover, it is a second object of the present invention to provide a film-shaped orally administered agent that can contain a broad range of types of drugs.

Furthermore, it is a third object of the present invention to provide an orally administered agent (in particular a film-shaped orally administered agent) according to which a drop in compliance of taking a drug due to the taste (e.g. bitterness, astringency) or smell of the drug can be prevented.

Furthermore, it is a fourth object of the present invention to provide an orally administered agent/supporting substrate complex according to which handling of an orally administered agent (e.g. carrying, storage etc. of the orally administered agent) can be made easy.

Furthermore, it is a fifth object of the present invention to provide an orally administered agent/supporting substrate complex according to which an orally administered agent can be administered easily.

Furthermore, it is a sixth object of the present invention to provide an orally administered agent/supporting substrate complex according to which it can easily be checked whether or not an orally administered agent has been taken.

Furthermore, it is a seventh object of the present invention to provide an orally administered pharmaceutical composition capable of completely masking the flavor, odor and the like of a drug contained in a drug-containing layer.

To attain the above objects, the present invention provides the following orally administered agent, the method of an administration of a drug and orally administered agent/supporting substrate complex.

(1) An orally administered agent comprising a drug-containing layer that contains a drug, a first water-swellable gel-forming layer that is provided on one side of said drug-containing layer, and a second water-swellable gel-forming layer that is provided on the other side of said drug-containing layer, wherein the first and second water-swellable gel-forming layers are formed from a composition that contains at least a water-swellable gel-forming agent, a film-forming agent, and a polyvalent metal compound as a cross-linking agent, the content of said water-swellable gel-forming agent in said composition is 13.5 to 70 wt %, and the content of said polyvalent metal compound in said composition is 1.5 to 5.6 wt %, and said drug is released in a stomach or an intestine from the orally administered agent after administration.

(2) The orally administered agent according to (1), wherein said orally administered agent is a film-shaped preparation.

(3) The orally administered agent according to (1), wherein said water-swellable gel-forming agent is a carboxyvinyl polymer.

(4) The orally administered agent according to (2), wherein said film-forming agent is at least one from a polyvinyl alcohol, polyvinyl pyrrolidone, hydroxyalkyl cellulose, and alkyl celluloses.

(5) The orally administered agent according to (1), wherein said polyvalent metal compound is at least one from calcium chloride, magnesium chloride, aluminum chloride, aluminum sulfate, aluminum potassium sulfate, iron chloride alum, ammonium alum, ferric sulfate, aluminum hydroxide, aluminum silicate, aluminum phosphate, iron citrate, magnesium oxide, calcium oxide, zinc oxide and zinc sulfate.

(6) The orally administered agent according to (1), wherein said first and second water-swellable gel-forming layers don't contain a drug.

(7) The orally administered agent according to (1), wherein said first and second water-swellable gel-forming layers are provided over the whole of the faces of said drug-containing layer.

(8) The orally administered agent according to (7), wherein said first and second water-swellable gel-forming layers are provided as an outermost layer of the orally administered agent.

(9) A method of an administration of a drug using an orally administered agent comprising a drug-containing layer that contains a drug, a first water-swellable gel-forming layer that is provided on one side of said drug-containing layer, and a second water-swellable gel-forming layer that is provided on the other side of said drug-containing layer, comprising a step of inserting said orally administered agent into a mouth without water, a step of swelling said water-swellable gel-forming layer by a saliva in the mouth, a step of swallowing the swelled orally administered agent, and a step of releasing the drug in a stomach or an intestine.

(10) The method of the administration of a drug according to (9), wherein said first and second water-swellable gel-forming layers are formed from a composition containing at least a water-swellable gel-forming agent, a film-forming agent and a polyvalent metal compound as a cross-linking agent, and the content of said water-swellable gel-forming agent in said composition is 13.5 to 70 wt %, and the content of the polyvalent metal compound in said composition is 1.5 to 5.6 wt %.

(11) The method of the administration of a drug according to (10), wherein said water-swellable gel-forming agent is a carboxyvinyl polymer.

(12) The method of the administration of a drug according to (10), wherein said film-forming agent is at least of one from a polyvinyl alcohol, polyvinyl pyrrolidone, hydroxyalkyl cellulose and alkyl celluloses.

(13) The method of the administration of a drug according to (10), wherein said polyvalent metal compound is at least of one from calcium chloride, magnesium chloride, aluminum chloride, aluminum sulfate, aluminum potassium sulfate, iron chloride alum, ammonium alum, ferric sulfate, aluminum hydroxide, aluminum silicate, aluminum phosphate, iron citrate, magnesium oxide, calcium oxide, zinc oxide and zinc sulfate.

(14) The method of the administration of a drug according to (9), wherein said first and second water-swellable gel-forming layers don't contain a drug.

(15) The method of the administration of a drug according to (9), wherein said orally administered agent is a film-shaped preparation.

(16) The method of the administration of a drug according to (9), wherein said first and second water-swellable gel-forming layers are provided over the whole of the faces of the drug-containing layer.

(17) The method of the administration of a drug according to (16), wherein said first and second water-swellable gel-forming layers are provided as an outermost layer of the orally administered agent.

(18) An orally administered agent/supporting substrate complex comprising a drug-containing layer that contains drug, an orally administered agent that contains a water-swellable gel-forming layer, and a supporting substrate that supports the orally administered agent, wherein said orally administered agent is provided on said supporting substrate either directly or via an intermediate layer, and said supporting substrate is composed of a soluble material that dissolves in a mouth.

(19) The orally administered agent/supporting substrate complex according to (18), wherein said supporting substrate has a gripping part and a mouth-inserting part, and said orally administered agent is provided on said mouth-inserting part.

BEST MODE FOR CARRYING OUT THE INVENTION

Figure 1:
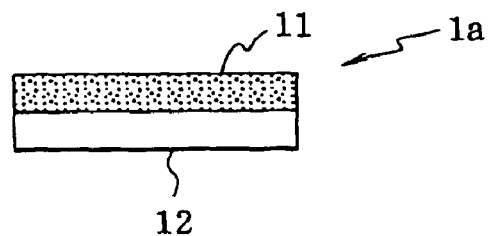
FIG. 1 is a sectional view showing an embodiment of the orally administered agent of the present invention for the case that one drug-containing layer is provided.

Following is a detailed description of the present invention.

First Embodiment

The orally administered agent of the present embodiment has drug-containing layer(s) and water-swellable gel-forming layer(s). The orally administered agent of the present embodiment may have layer(s) other than the drug-containing layer(s) and the water-swellable gel-forming layer(s), or may be constituted from only the drug-containing layer(s) and the water-swellable gel-forming layer(s).

The orally administered agent of the present embodiment is a layered medicinal agent constituted from a plurality of layers built up on one another; however, the orally administered agent is not limited to having a flat shape as with a film-shaped preparation (sheet-shaped preparation), but rather so long as the orally administered agent is layered, the orally administered agent may have any shape. For example, the shape may be a shape formed by folding up a flat shape (see FIG. 6).

The orally administered agent of the present embodiment is preferably a film-shaped preparation. By processing into a film-shaped preparation, the moisture content in the preparation can be kept low, and hence the stability of the drug contained in the preparation can be increased (particularly in the case of a readily hydrolyzable drug). Moreover, handling of the preparation becomes easy, and the packaging cost can be reduced.

In the case that the orally administered agent of the present embodiment is film-shaped, layer(s) for adjusting the film thickness may be provided as layer(s) other than the drug-containing layer(s) and the water-swellable gel-forming layer(s). By providing such layer(s) and thus increasing the film thickness, the ease of handling of the orally administered agent of the present embodiment can be improved.

In the orally administered agent of the present embodiment, 'drug-containing layer' means a layer containing the drug to be administered. The thickness of the drug-containing layer(s) can be adjusted as appropriate in accordance with the drug content and so on within a thickness range for which oral administration can be carried out; in the case of making into a film-shaped preparation, the thickness of the drug-containing layer(s) is preferably 0.1 to 1000 µm, more preferably 10 to 200 µm. This is because if the thickness of the drug-containing layer(s) is less than 0.1 µm, then it will be difficult to make the film with good precision (i.e. variation will arise in the drug content in the drug-containing layer(s)); on the other hand, if the thickness of the drug-containing layer(s) exceeds 1000 µm, then the film will become stiff and hence taking the agent will become difficult.

A single drug-containing layer may be provided in the orally administered agent of the present embodiment, or a plurality of drug-containing layers may be provided. In the case of providing a plurality of drug-containing layers in the orally administered agent of the present embodiment, the drug-containing layers may be laminated together directly, or may be laminated together via intermediate layer(s). Moreover, a single drug-containing layer may be formed from a plurality of drug-containing layers formed side by side (see FIG. 3).

The drug-containing layer(s) may comprise only the drug to be administered, but usually contain additive(s) such as pharmacologically acceptable excipient(s), binder(s) and disintegrator(s) as a base for keeping the drug to be administered in a desired state in the drug-containing layer. Moreover, masking agent(s), colorant(s) and so on may be included in the drug-containing layer(s) as described later.

There are no particular limitations on a base contained along with the drug in the drug-containing layer(s); a base can be selected as appropriate in accordance with the object of adding the base. Specific examples of bases that may be contained in the drug-containing layer(s) include cellulose and derivatives thereof, for example crystalline cellulose, carboxymethyl cellulose, hydroxypropyl cellulose, hydroxypropyl methyl cellulose, methyl cellulose, ethyl cellulose, cellulose acetate, cellulose acetate phthalate, hydroxypropyl methyl cellulose phthalate, hydroxypropyl methyl cellulose acetate succinate, and carboxymethyl ethyl cellulose, or pharmacologically acceptable salts thereof (e.g. a sodium salt); starches and derivatives thereof, for example α-starch, oxidized starch, sodium carboxymethyl starch, hydroxypropyl starch, dextrin, and dextran; saccharides, for example saccharose, maltose, lactose, glucose, fructose, pullulan, xanthan gum, and cyclodextrin; sugar alcohols, for example xylitol, mannitol, and sorbitol; acrylic acid derivatives, for example a dimethylaminoethyl methacrylate—methacrylic acid copolymer, a methacrylic acid—ethyl acrylate copolymer, a methacrylic acid—methyl methacrylate copolymer, an ethyl methacrylate—trimethylammonium methacrylate chloride copolymer, a dimethylaminoethyl methacrylate—methacrylate methyl chloride copolymer, and a methacrylic acid—acrylate ethyl chloride copolymer; shellac; polyvinyl acetal diethylamino acetate; vinyl acetate; polyvinyl alcohol; polyvinyl pyrrolidone; natural rubber, for example gum arabic, and tragacanth gum; polyglucosamines, for example chitin, and chitosan; proteins, for example gelatin, casein, and soy protein; titanium oxide; calcium monohydrogen phosphate; calcium carbonate; talc; stearates; magnesium aluminate metasilicate; magnesium silicate; and silicic anhydride; these can be used singly or two or more can be used in combination.

It is preferable for a base contained in the drug-containing layer(s) to be an edible polymer. The edible polymer may be a synthetic polymer or a natural polymer, and there are no particular limitations on the type thereof.

The edible polymer is preferably a stomach-soluble polymer or an intestine-soluble polymer.

Out of edible polymers, examples of preferable ones are cellulose and/or cellulose derivatives, and examples of particularly preferable ones include hydroxypropyl cellulose, and hydroxypropyl methyl cellulose phthalate. Hydroxypropyl cellulose and hydroxypropyl methyl cellulose phthalate have excellent film-forming properties, and hence are particularly useful in the case of making the drug-containing layer(s) film-shaped. By making the drug-containing layer(s) film-shaped, it becomes possible to make the orally administered agent of the present embodiment as a whole film-shaped.

The content of the edible polymer in each drug-containing layer is an amount such that formation of the layer is possible; this amount can be adjusted as appropriate in accordance with the type of the edible polymer and so on, but is usually at least 20 wt %, preferably at least 60 wt %, more preferably at least 70 wt %, of the drug-containing layer. If the edible polymer content is less than 20 wt %, then the formation of the drug-containing layer will be inadequate. Note that the upper limit of the content of the edible polymer in the drug-containing layer is the value obtained by subtracting the minimum content of the drug in the drug-containing layer from 100 wt %, and is set as appropriate in accordance with the type of the drug and so on.

The drug contained in each drug-containing layer is a drug that is to be administered to the patient or the like, and so long as it is a drug that can be orally administered, there are no particular limitations thereon. Examples of drugs that can be orally administered include: as drugs that act on the central nervous system: hypnotics such as amobarbital, estazolam, triazolam, nitrazepam, and pentobarbital; psychotropic agents such as amitriptyline hydrochloride, imipramine hydrochloride, oxazolam, chlordiazepoxide, chlorpromazine, diazepam, sulpiride, and haloperidol; antiparkinsonism agents such as trihexyphenidyl, and levodopa; analgesics and antiphlogistics such as aspirin, isopropyl antipyrine, indomethacin, diclofenac sodium, mefenamic acid, streptokinase, streptodornase, serrapeptase, and pronase; and central nervous metabolism activators such as ATP, and vinpocetine; as drugs that act on the respiratory organs: expectorants such as carbocysteine, and bromhexine hydrochloride; and antiasthmatic agents such as azelastine hydrochloride, oxatomide, theophylline, terbutaline sulfate, tranilast, procaterol hydrochloride, and ketotifen fumarate; as drugs that act on the circulatory system: cardiotonics such as aminophylline, digitoxin, and digoxin; antiarrhythmic agents such as ajmaline, disopyramide, procainamide hydrochloride, and mexiletine hydrochloride; antianginal agents such as amyl nitrite, alprenolol hydrochloride, isosorbide nitrate, nicorandil, oxyfedrine, dipyridamole, dilazep hydrochloride, diltiazem hydrochloride, nitroglycerine, nifedipine, and verapamil hydrochloride; peripheral vasodilators such as kallidinogenase; antihypertensive agents such as atenolol, captopril, clonidine hydrochloride, metoprolol tartrate, spironolactone, triamterene, trichlormethazide, nicardipine, hydralazine hydrochloride, hydrochlorothiazide, prazosin hydrochloride, furosemide, propranolol hydrochloride, enalapril maleate, methyldopa, labetalol hydrochloride, and reserpine; and anti-arteriosclerotic agents such as clofibrate, dextran sulfate, nicomol, and niceritrol; as drugs that act on the blood or have a hemopoietic action: hemostatics such as carbazochrome sodium sulfonate, and tranexamic acid; antithrombotic agents such as ticlopidine hydrochloride, and warfarin potassium; and therapeutic drugs for anemia such as iron sulfate; as drugs that act on the digestive system: antiulcer agents such as azulene, aldioxa, cimetidine, ranitidine hydrochloride, famotidine, teprenone, and rebamipide; antiemetics such as domperidone, and metoclopramide; evacuants such as sennoside; digestive enzyme preparations; and therapeutic drugs for liver disorders such as glycyrrhizin, and liver extract preparations; as drugs that act on metabolic disorders: antidiabetic agents such as glibenclamide, chlorpropamide, and tolbutamide; therapeutic drugs for gout such as allopurinol, and colchicine; as a drug in the opthalmological field: acetazolamide; as drugs in the otorhinological field: anti-vertigo drugs such as difenidol hydrochloride, and betahistine mesilate; as chemotherapeutic agents and antibiotics: isoniazid, ethambutol hydrochloride, ofloxacin, erythromycin stearate, cefaclor, norfloxacin, fosfomycin calcium, minocycline hydrochloride, rifampicin, rokitamycin, etc.; as drugs against malignant tumors: cyclophosphamide, tegafur etc.; as immunosuppressants: azathioprine, etc.; as hormones and endocrine therapeutic drugs: progesterone, salivary gland hormone, thiamazole, prednisolone, betamethasone, liothyronine, levothyroxine, etc.; and as autacoids: antihistamines such as clemastine fumarate, and d-chlorpheniramine maleate; and vitamins such as alfacalcidol, cobamamide, tocopherol nicotinate, and mecobalamin.

There are no particular limitations on the content of the drug in each drug-containing layer; this content can be adjusted as appropriate in accordance with the type of the drug, but is usually not more than 80 wt %, preferably not more than 40 wt %, more preferably not more than 30 wt %, of the drug-containing layer. If the content of the drug exceeds 80 wt %, then the film strength of the film-shaped preparation will drop. Note that the lower limit of the drug content in the drug-containing layer is set as appropriate in accordance with the type of the drug in the drug-containing layer, and is usually about 0.001 wt %.

A broad range of types of drugs from drugs for which the dose is minute to drugs for which the dose is large can be contained in the drug-containing layer(s). Here, the dose being minute means that a single dose is 1 mg or less, and the dose being large means that a single dose is 300 mg or more.

Even in the case that the orally administered agent of the present embodiment is a film-shaped preparation, a broad range of types of drugs from drugs for which the dose is minute to drugs for which the dose is large, or insoluble bulky drugs that are prone to bringing about a drop in the film strength, can be contained in the drug-containing layer(s). This is because the drug-containing layer(s) and the water-swellable gel-forming layer(s) are formed as separate layers, and hence even if the drug content in the drug-containing layer(s) increases and thus the film strength of the drug-containing layer(s) drops, the strength of the film-shaped preparation as a whole can still be maintained by giving the water-swellable gel-forming layer(s) film-forming properties. The film-shaped orally administered agent of the present embodiment is thus particularly useful with the administration of a drug for which the dose is large or a bulky drug.

In the orally administered agent of the present embodiment, 'water-swellable gel-forming layer' means a layer that contains a water-swellable gel-forming agent, and is thus able to swell through moisture to form a gel. The thickness of the water-swellable gel-forming layer(s) can be adjusted as appropriate within a thickness range for which oral administration can be carried out; in the case of making into a film-shaped preparation, the thickness of the water-swellable gel-forming layer(s) is preferably 10 to 1000 μm, more preferably 20 to 500 μm. If the thickness of the water-swellable gel-forming layer(s) is less than 10 μm, then gel formation will be inadequate, and masking of the taste and/or smell of the drug by the water-swellable gel-forming layer(s) will be inadequate; on the other hand, if the thickness of the water-swellable gel-forming layer(s) exceeds 1000 μm, then it will not be possible for swelling and gel formation to take place sufficiently just through saliva upon administration into the mouth of a patient or the like, and hence taking the agent will become difficult.

In the orally administered agent of the present embodiment, the water-swellable gel-forming layer is preferably formed from a composition that contains at least a water-swellable gel-forming agent, a film-forming agent, and a polyvalent metal compound as a cross-linking agent.

The content of the water-swellable gel-forming agent in the composition is preferably 13.5 to 70 wt %, more preferably 15 to 50 wt %. The content of the polyvalent metal compound in the composition is preferably 1.5 to 5.6 wt %, more preferably 3.0 to 5.6 wt %.

The ratio of the content by weight of the polyvalent metal compound and the content by weight of the water-swellable gel-forming agent in the composition is preferably 3:100 to 16.7:100, more preferably 6:100 to 16.7:100.

The content of the film-forming agent in the composition is preferably 24.4 to 85 wt %, more preferably 44.4 to 70 wt %.

There are no particular limitations on the type of the water-swellable gel-forming agent providing that it is capable of swelling through moisture to form a gel; the water-swellable gel-forming agent may be a cross-linked one or a non-cross-linked one. Specific examples of the water-swellable gel-forming agent include carboxyvinyl polymers, starches and derivatives thereof, agar, alginic acid, arabinogalactan, galactomannan, cellulose and derivatives thereof, carrageen, dextran, tragacanth, gelatin, pectin, hyaluronic acid, gellan gum, collagen, casein, and xanthan gum.

Out of these water-swellable gel-forming agents, a cross-linked carboxyvinyl polymer is preferable, with cross-linked polyacrylic acid being particularly preferable. A cross-linked carboxyvinyl polymer, and in particular cross-linked polyacrylic acid, does not exert adverse effects on the film-forming ability of the film-forming agent, and is capable of exhibiting a suitable gel strength upon swelling.

Cross-linking can be carried out using a cross-linking agent in accordance with the type of molecule to be cross-linked. A carboxyvinyl polymer can be cross-linked using, for example, a polyvalent metal compound. Specific examples of such a polyvalent metal compound include calcium chloride, magnesium chloride, aluminum chloride, aluminum sulfate, aluminum potassium sulfate, iron chloride alum, ammonium alum, ferric sulfate, aluminum hydroxide, aluminum silicate, aluminum phosphate, iron citrate, magnesium oxide, calcium oxide, zinc oxide, and zinc sulfate.

In the case of making the orally administered agent of the present embodiment into a film-shaped preparation, the water-swellable gel-forming layer(s) must be made film-shaped; in this case, to improve the film-forming properties of the water-swellable gel-forming layer(s), it is preferable to include a film-forming agent in the water-swellable gel-forming layer(s).

So long as the film-forming agent has a film-forming ability, there are no particular limitations on the type thereof. Specific examples of the film-forming agent include polyvinyl alcohol, polyvinyl pyrrolidone, polyvinyl acetate, polyvinyl acetate phthalate, hydroxyalkyl celluloses (e.g. hydroxypropyl cellulose, hydroxypropyl methyl cellulose, hydroxymethyl cellulose, hydroxyethyl cellulose), alkyl celluloses (e.g. methyl cellulose, ethyl cellulose), carboxyalkyl celluloses (e.g. carboxymethyl cellulose), (meth)acrylic acid and esters thereof, xanthan gum, carrageenan, and alginic acid.

The film-forming agent is preferably water-soluble. This is because in the case that the film-forming agent is water-soluble, it becomes easy for moisture to infiltrate into the water-swellable gel-forming layer(s), and hence swelling of the water-swellable gel-forming layer(s) to form a gel can be made to occur rapidly in the mouth.

Examples of water-soluble film-forming agents include polyvinyl alcohol; hydroxyalkyl celluloses such as hydroxypropyl cellulose, and hydroxypropyl methyl cellulose; polyvinyl pyrrolidone; xanthan gum; carrageenan; and alginic acid.

To give the water-swellable gel-forming layer(s) a suitable pliability, a plasticizer may be included in the water-swellable gel-forming layer(s). Examples of such a plasticizer include propylene glycol, polyethylene glycol, glycerin and sorbitol, glycerin triacetate, diethyl phthalate and triethyl citrate, lauric acid, saccharose, and sorbitol. Note that such a plasticizer may also be included in the drug-containing layer(s), and in intermediate layer(s), mentioned later, as well as in the water-swellable gel-forming layer(s).

Moreover, a masking agent for masking the taste or smell of the drug in the drug-containing layer(s) may be included in the water-swellable gel-forming layer(s). By including a masking agent in the water-swellable gel-forming layer(s), the effect of the water-swellable gel-forming layer(s) masking the taste or smell of the drug can be improved, and hence a drop in compliance of taking the drug can be efficiently prevented.

As a masking agent, for example an agent giving an acid taste such as citric acid, tartaric acid or fumaric acid, a sweetening agent such as saccharin, glycyrrhizinic acid, saccharose, fructose or mannitol, a refrigerative such as menthol, mint oil, peppermint or spearmint, or a natural or synthetic flavoring can be used.

In the case that polyvinyl alcohol or the like is contained in the water-swellable gel-forming layer(s) as a film-forming agent, this film-forming agent will also be able to fulfil the role of a masking agent. In this way, it is preferable to use a film-forming agent having a masking action, and it is similarly preferable to use a water-swellable gel-forming agent having a masking action.

Moreover, preservatives such as methyl hydroxybenzonate and propyl hydroxybenzonate, colorants such as edible lake colorants, and so on may also be included in the water-swellable gel-forming layer(s).

In general the introduction of such additives causes a reduction in the strength of the film-shaped water-swellable gel-forming layer(s), and as a result it becomes easier for moisture to infiltrate into the water-swellable gel-forming layer(s), and hence it becomes easier for swelling of the water-swellable gel-forming agent and thus gel formation to take place through moisture that has infiltrated into the water-swellable gel-forming layer(s).

In the orally administered agent of the present embodiment, water-swellable gel-forming layer(s) is/are provided as outermost layer(s).

So long as water-swellable gel-forming layer(s) is/are provided as outermost layer(s) of the orally administered agent of the present embodiment, the water-swellable gel-forming layer(s) may be provided over the whole of the faces (or almost the whole of the faces) of the orally administered agent of the present embodiment, or may be provided on some of the faces of the orally administered agent; however, from the standpoint of efficiently exhibiting the effects of the water-swellable gel-forming layer(s) (improving the ease and safety of taking the agent, preventing a drop in compliance of taking the drug, etc.), it is preferable for the water-swellable gel-forming layer(s) to be provided over the whole of the faces (or almost the whole of the faces) of the orally administered agent of the present embodiment. For example, in the case that the orally administered agent of the present embodiment is a film-shaped preparation, out of the two outside faces of the film-shaped preparation, either one face or both faces can be made to be a water-swellable gel-forming layer, but it is preferable to make both faces a water-swellable gel-forming layer.

Here, 'outermost layer' means a layer that constitutes an outside face of the orally administered agent of the present embodiment when the orally administered agent of the present embodiment is inside the mouth of a patient or the like. 'Outermost layer' thus obviously includes a layer that constitutes an outside face of the orally administered agent of the present embodiment before administration, but also includes a layer that does not constitute an outside face of the orally administered agent of the present embodiment before administration but does constitute an outside face of the orally administered agent of the present embodiment when the orally administered agent is inside the mouth of a patient or the like. For example, even in the case that another layer is provided as a layer further to the outside than a water-swellable gel-forming layer, if this outer layer disintegrates or dissolves through moisture in saliva or the like inside the mouth of the patient or the like, then the water-swellable gel-forming layer comes to constitute an outside face of the orally administered agent of the present embodiment when the orally administered agent is inside the mouth of the patient, and hence this means that the water-swellable gel-forming layer is provided as an 'outermost layer' of the orally administered agent of the present embodiment.

So long as water-swellable gel-forming layer(s) constitute outside face(s) of the orally administered agent of the present embodiment when the orally administered agent of the present embodiment is inside the mouth of a patient or the like, only one water-swellable gel-forming layer may be provided in the orally administered agent of the present embodiment, or a plurality of water-swellable gel-forming layers may be provided.

In the case that one drug-containing layer is provided in the orally administered agent of the present embodiment, for example a water-swellable gel-forming layer can be provided either on one face or on both faces of the drug-containing layer, this being either directly or via an intermediate layer.

One embodiment of the form of the agent for the case that one drug-containing layer is provided is shown in FIG. 1. As shown in FIG. 1, the orally administered agent 1a has one drug-containing layer 11 and one water-swellable gel-forming layer 12, with the water-swellable gel-forming layer 12 being provided directly on one face of the drug-containing layer 11.

Figure 2:
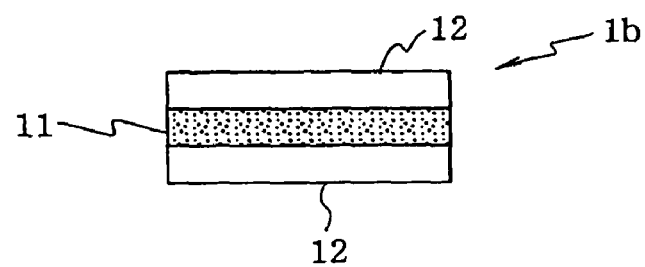
FIG. 2 is a sectional view showing another embodiment of the orally administered agent of the present invention for the case that one drug-containing layer is provided.

Moreover, another embodiment for the case that one drug-containing layer is provided is shown in FIG. 2. As shown in FIG. 2, the orally administered agent 1b has one drug-containing layer 11 and two water-swellable gel-forming layers 12, with the water-swellable gel-forming layers 12 being provided directly on both faces of the drug-containing layer 11.

Figure 3:
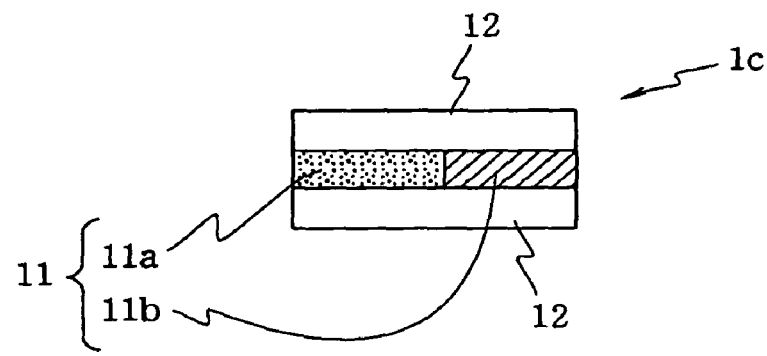
FIG. 3 is a sectional view showing another embodiment of the orally administered agent of the present invention for the case that one drug-containing layer is provided.

Moreover, another embodiment for the case that one drug-containing layer is provided is shown in FIG. 3. As shown in FIG. 3, the orally administered agent 1c has one drug-containing layer 11 that comprises a drug-containing layer 11a and a drug-containing layer 11b that are formed side by side, and two water-swellable gel-forming layers 12, with the water-swellable gel-forming layers 12 being provided directly on both faces of the drug-containing layer 11.

Figure 4:
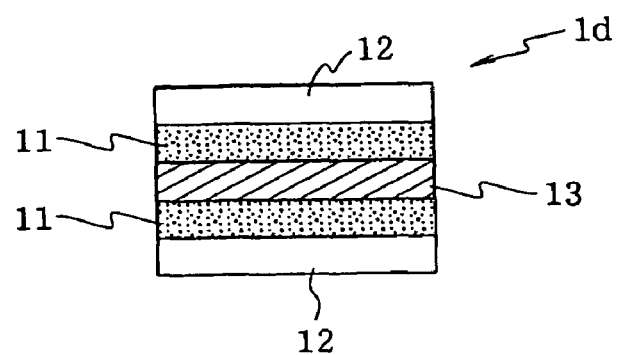
FIG. 4 is a sectional view showing an embodiment of the orally administered agent of the present invention for the case that two drug-containing layers are provided.

In the case that a plurality of drug-containing layers are provided in the orally administered agent of the present embodiment, for example water-swellable gel-forming layer(s) can each be provided, either directly or via an intermediate layer, on the outside face of a drug-containing layer positioned most to the outside (i.e. the face of this drug-containing layer on the opposite side to the face that is in contact with an intermediate layer or another drug-containing layer). One embodiment of the form of the agent for the case that a plurality of drug-containing layers are provided is shown in FIG. 4. As shown in FIG. 4, the orally administered agent 1d has two drug-containing layers 11, two water-swellable gel-forming layers 12, and one intermediate layer 13; the two drug-containing layers 11 are laminated together via the intermediate layer 13, and each water-swellable gel-forming layer 12 is directly provided on the outside face of one of the two drug-containing layers 11 (i.e. the face of this drug-containing layer 11 on the opposite side to the face that is in contact with the intermediate layer 13).

Figure 5:
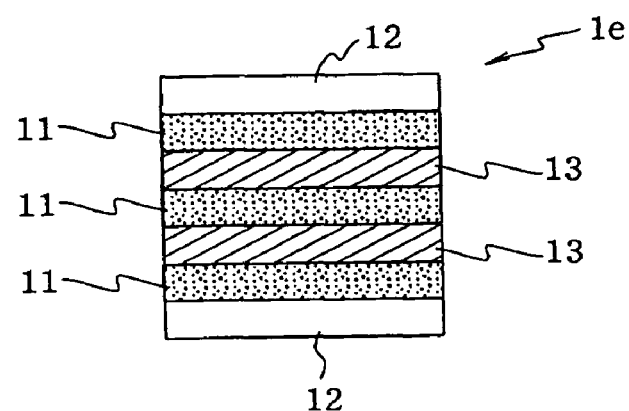
FIG. 5 is a sectional view showing an embodiment of the orally administered agent of the present invention for the case that three drug-containing layers are provided.

Moreover, another embodiment for the case that a plurality of drug-containing layers are provided is shown in FIG. 5. As shown in FIG. 5, the orally administered agent 1e has three drug-containing layers 11, two water-swellable gel-forming layers 12, and two intermediate layers 13; the three drug-containing layers 11 are laminated together via the intermediate layers 13, and each water-swellable gel-forming layer 12 is directly provided on the outside face of one of the three drug-containing layers 11 that is positioned most to the outside (i.e. the uppermost drug-containing layer or the lowermost drug-containing layer in FIG. 5) (i.e. the face of this drug-containing layer 11 on the opposite side to the face that is in contact with one of the intermediate layers 13).

In the orally administered agents 1a to 1e shown in FIGS. 1 to 5, the water-swellable gel-forming layer(s) 12 may each be provided on the respective drug-containing layer 11 via an intermediate layer.

Intermediate layer(s) can be provided between the layers that constitute the orally administered agent of the present embodiment (e.g. between a drug-containing layer and a water-swellable gel-forming layer, between two drug-containing layers, between a water-swellable gel-forming layer or a drug-containing layer and a supporting substrate); the constituents of the intermediate layer(s) can be selected as appropriate in accordance with the purpose. For example, in the case of providing an intermediate layer with a purpose of bonding two layers together, a pharmacologically acceptable adhesive is included. Out of such adhesives, specific examples of adhesives that exhibit adhesiveness when used in a state containing a solvent include carboxyvinyl polymers, polyacrylic acid and pharmacologically acceptable non-toxic salts thereof such as sodium polyacrylate, acrylic acid copolymers and pharmacologically acceptable salts thereof, hydrophilic cellulose derivatives such as carboxymethyl cellulose and sodium salts, pullulan, povidone, karaya gum, pectin, xanthan gum, tragacanth, alginic acid, gum arabic, and acidic polysaccharides and derivatives or pharmacologically acceptable salts thereof; specific examples of adhesives that exhibit adhesiveness when heated (i.e. heat-sealing adhesives) include a homopolymer of vinyl acetate, and a copolymer between vinyl acetate and vinyl pyrrolidone.

In the orally administered agent of the present embodiment, because the water-swellable gel-forming layer(s) is/are provided as outermost layer(s), the water-swellable gel-forming layer(s) swell through moisture in saliva or the like in the mouth of a patient or the like to form a gel. As a result, the orally administered agent of the present embodiment changes into a form having a size, shape, elasticity, viscosity and so on such that swallowing is easy; the orally administered agent can thus be easily taken, and moreover the risk of the orally administered agent getting stuck in the trachea of the patient or the like is reduced, and thus the orally administered agent can be taken safely even by an elderly person or an infant. Moreover, in the case of a patient or the like who has little saliva and hence the water-swellable gel-forming layer(s) do not swell and form a gel sufficiently, the same effects can be produced by making the patient or the like take the orally administered agent with a little water, or by dipping the orally administered agent in water before administration. The amount of water required in this case is very small compared with the amount of water required when taking a solid preparation such as a tablet or a capsule.

Figure 6:
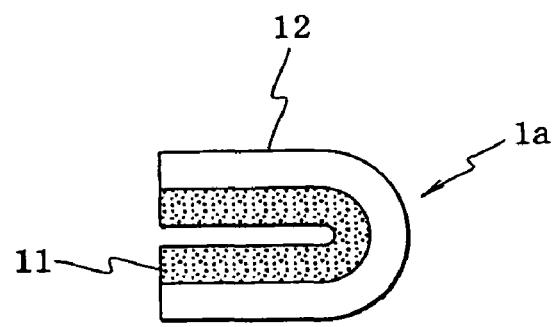
FIG. 6 is a sectional view showing the state of the orally administered agent shown in FIG. 1 during administration.

Moreover, in the orally administered agent of the present embodiment, because the water-swellable gel-forming layer(s) is/are provided as outermost layer(s), the orally administered agent can be administered to a patient or the like in a state in which the whole (or almost the whole) of the outside faces of the orally administered agent is covered by the water-swellable gel-forming layer(s); as a result, the taste (e.g. bitterness, astringency) or smell of the drug in the drug-containing layer is masked, and hence a drop in compliance of taking the drug can be prevented. For example, in the case of the form of the agent shown in FIG. 1, by administering the orally administered agent 1a folded in two so that the whole (or almost the whole) of the outside faces of the orally administered agent 1a is covered by the water-swellable gel-forming layer 12 as shown in FIG. 6, the taste or smell of the drug in the drug-containing layer 11 can be masked. Moreover, in the cases of the forms of the agent shown in FIGS. 2 to 5, because the whole (or almost the whole) of the outside faces of the orally administered agent 1b, 1c, 1d or 1e is covered by the water-swellable gel-forming layers 12, if the orally administered agent is administered as it is, then the taste or smell of the drug in the drug-containing layer 11 can be masked.

The orally administered agent of the present embodiment can be supported on a supporting substrate. In an orally administered agent/supporting substrate complex of the present embodiment, the orally administered agent of the present embodiment is provided on the supporting substrate either directly or via an intermediate layer. By supporting the orally administered agent of the present embodiment on a supporting substrate in this way, handling of the orally administered agent of the present embodiment (e.g. carrying, storage etc. of the orally administered agent) becomes easy. Moreover, by forming the orally administered agent of the present embodiment on a supporting substrate, manufacture of the orally administered agent of the present embodiment becomes easy.

Figure 7:
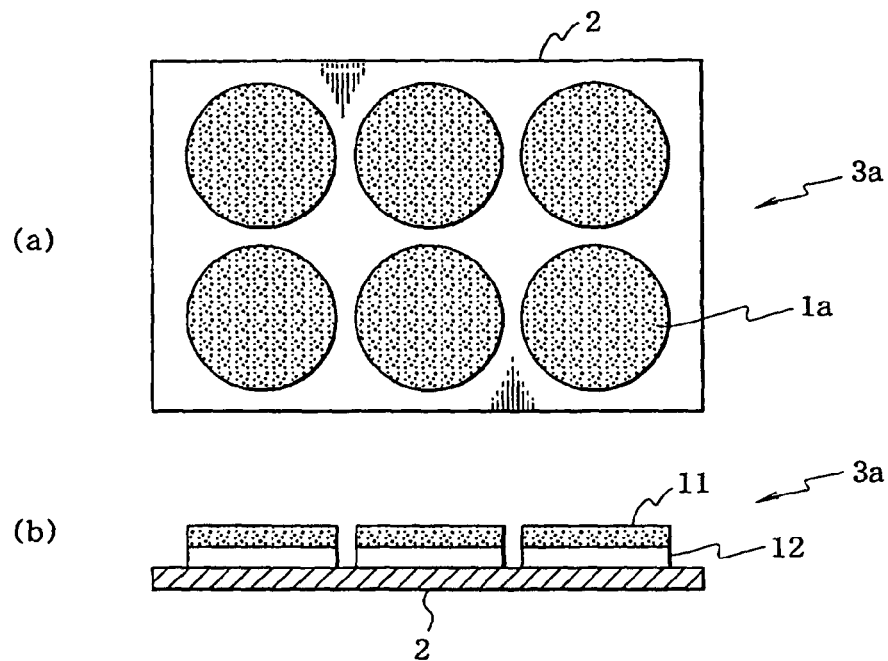
FIG. 7(a) is a top view showing an embodiment of the orally administered agent/supporting substrate complex of the present invention.
FIG. 7(b) is a sectional view showing this embodiment.

An embodiment of the orally administered agent/supporting substrate complex of the present embodiment is shown in FIG. 7. Note that FIG. 7(a) is a top view of the orally administered agent/supporting substrate complex according to this embodiment, and FIG. 7(b) is a sectional view of the orally administered agent/supporting substrate complex according to this embodiment.

The orally administered agent/supporting substrate complex 3a shown in FIG. 7 has, on a sheet-shaped supporting substrate 2, orally administered agents 1a each comprising a drug-containing layer 11 and a water-swellable gel-forming layer 12; the drug-containing layer 11 of each orally administered agent 1a is provided on one face of the sheet-shaped supporting substrate 2 via the water-swellable gel-forming layer 12. In the orally administered agent support 3a, orally administered agents 1a may also be provided on both faces of the sheet-shaped supporting substrate 2. Moreover, in the orally administered agent/supporting substrate complex 3a shown in FIG. 7, the number of orally administered agents 1a supported on the sheet-shaped supporting substrate 2 is six, but this number can be changed as appropriate.

Figure 8:
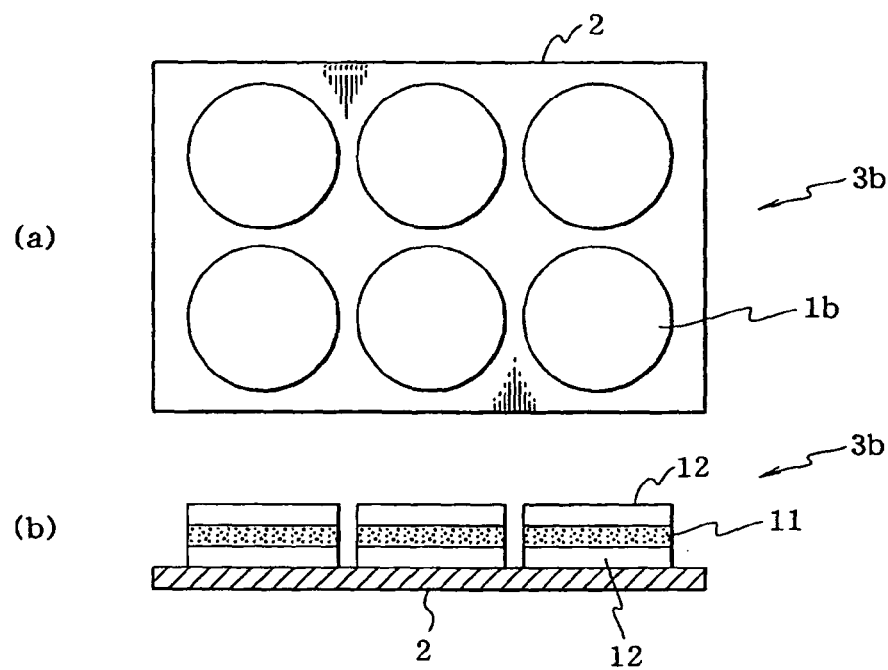
FIG. 8(a) is a top view showing another embodiment of the orally administered agent/supporting substrate complex of the present invention.
FIG. 8(b) is a sectional view showing this embodiment.

Moreover, another embodiment of the orally administered agent/supporting substrate complex of the present embodiment is shown in FIG. 8. Note that FIG. 8(a) is a top view of the orally administered agent/supporting substrate complex according to this embodiment, and FIG. 8(b) is a sectional view of the orally administered agent/supporting substrate complex according to this embodiment.

The orally administered agent/supporting substrate complex 3b shown in FIG. 8 has, on a sheet-shaped supporting substrate 2, orally administered agents 1b each constituted such that a drug-containing layer 11 is sandwiched between water-swellable gel-forming layers 12; the orally administered agents 1b are provided on one face of the sheet-shaped supporting substrate 2 via the water-swellable gel-forming layers 12. In the orally administered agent/supporting substrate complex 3b, orally administered agents 1b may also be provided on both faces of the sheet-shaped supporting substrate 2. Moreover, in the orally administered agent/supporting substrate complex 3b shown in FIG. 8, the number of orally administered agents 1b supported on the sheet-shaped supporting substrate 2 is six, but this number can be changed as appropriate.

In the orally administered agent/supporting substrate complex of the present embodiment, there are no particular limitations on the material of the supporting substrate, provided that this material can be molded; either an insoluble material that does not dissolve in the mouth of a patient or the like, or a soluble material that does dissolve in the mouth of a patient or the like may be used. As an insoluble material, for example a plastic such as polyethylene terephthalate, polyethylene, polypropylene or polyvinyl acetate, or paper or the like can be used. Moreover, as a soluble material, for example edible polymers such as polyvinyl alcohol, polyvinyl pyrrolidone, hydroxyalkyl celluloses (e.g. hydroxypropyl cellulose, hydroxypropyl methyl cellulose, hydroxymethyl cellulose, hydroxyethyl cellulose), alkyl celluloses (e.g. methyl cellulose, ethyl cellulose), carboxyalkyl celluloses (e.g. carboxymethyl cellulose), (meth)acrylic acid and esters thereof, carboxyvinyl polymers, starches and derivatives thereof, agar, alginic acid, arabinogalactan, galactomannan, cellulose and derivatives thereof, carrageen, dextran and tragacanth can each be used alone or two or more thereof can be used in combination.

There are no particular limitations on the shape of the supporting substrate, but the supporting substrate is preferably sheet-shaped, more preferably the sheet-shaped supporting substrate has a gripping part and a mouth-inserting part, with the orally administered agent of the present embodiment being provided on the mouth-inserting part.

Figure 9:
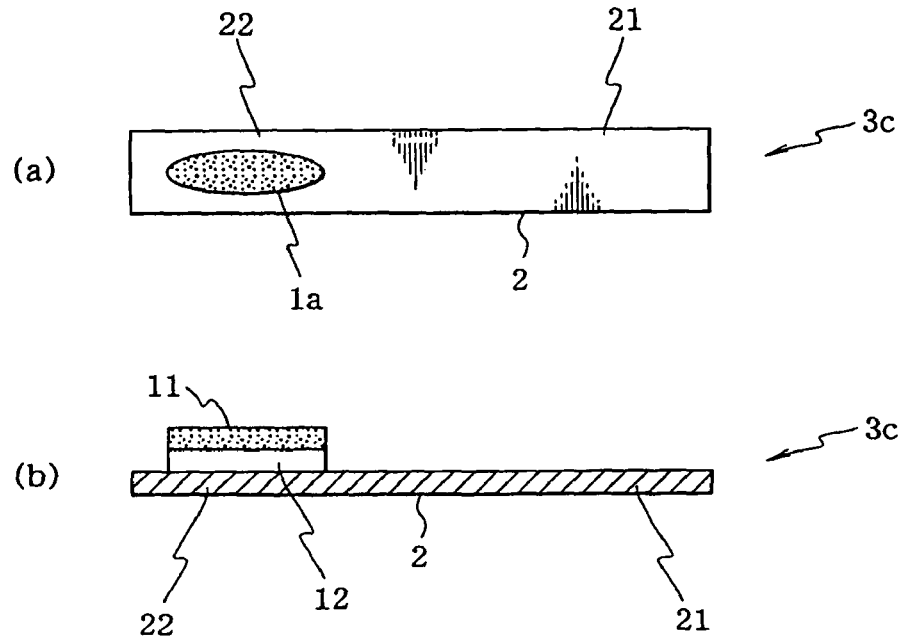
FIG. 9(a) is a top view showing yet another embodiment of the orally administered agent/supporting substrate complex of the present invention.
FIG. 9(b) is a sectional view showing this embodiment.

An embodiment of an orally administered agent/supporting substrate complex comprising a sheet-shaped supporting substrate having a gripping part and a mouth-inserting part is shown in FIG. 9. Note that FIG. 9(a) is a top view of the orally administered agent/supporting substrate complex according to this embodiment, and FIG. 9(b) is a sectional view of the orally administered agent/supporting substrate complex according to this embodiment.

The orally administered agent/supporting substrate complex 3c shown in FIG. 9 has a supporting substrate 2 having a gripping part 21 and a mouth-inserting part 22, and an orally administered agent 1a that is supported on the mouth-inserting part 22 of the supporting substrate 2.

Figure 10:
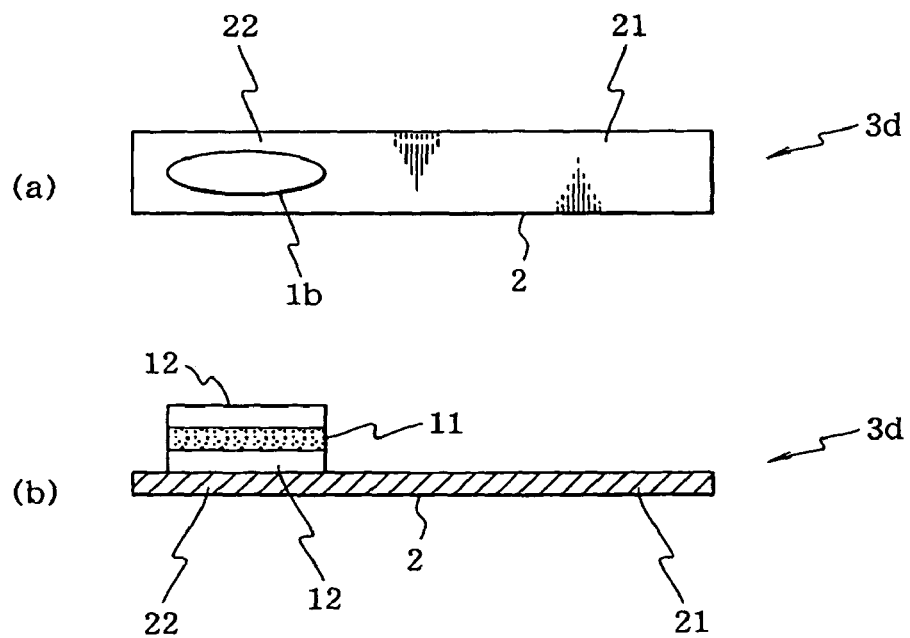
FIG. 10(a) is a top view showing yet another embodiment of the orally administered agent/supporting substrate complex of the present invention.
FIG. 10(b) is a sectional view showing this embodiment.

Moreover, another embodiment of the orally administered agent/supporting substrate complex comprising a sheet-shaped supporting substrate having a gripping part and a mouth-inserting part is shown in FIG. 10. Note that FIG. 10(a) is a top view of the orally administered agent/supporting substrate complex according to this embodiment, and FIG. 10(b) is a sectional view of the orally administered agent/supporting substrate complex according to this embodiment.

The orally administered agent/supporting substrate complex 3d shown in FIG. 10 has a supporting substrate 2 having a gripping part 21 and a mouth-inserting part 22, and an orally administered agent 1b that is supported on the mouth-inserting part 22 of the supporting substrate 2. The supporting substrate 2 of the orally administered agent/supporting substrate complexes 3c and 3d has a strip shape in which the gripping part 21 and the mouth-inserting part 22 are molded as a single body. In the orally administered agent/supporting substrate complexes 3c and 3d, the number of orally administered agents 1a or 1b supported on the supporting substrate 2 is one, but this number can be changed as appropriate.

In the supporting substrate, the gripping part and the mouth-inserting part may be formed as a single body, or may be formed separately to one another. There are no particular limitations on the shape, structure, size and so on of the gripping part provided that the gripping part can be grasped with the hand, and there are no particular limitations on the shape, structure, size and so on of the mouth-inserting part provided the mouth-inserting part can support the orally administered agent of the present embodiment and can be inserted into the mouth of a patient or the like.

According to the orally administered agent/supporting substrate complex comprising a supporting substrate having a gripping part and a mouth-inserting part in this way, by holding the gripping part of the supporting substrate with the hand, and inserting the mouth-inserting part on which the orally administered agent of the present embodiment is supported into the mouth of a patient or the like, the orally administered agent of the present embodiment can easily be administered. Moreover, by taking the mouth-inserting part out from the mouth of the patient or the like, and checking for the presence/absence of the orally administered agent of the present embodiment on the mouth-inserting part, it can easily be checked visually whether or not the agent has been taken.

In the case that the supporting substrate is constituted from a soluble material that dissolves in the mouth, by inserting the mouth-inserting part on which the orally administered agent of the present embodiment is supported into the mouth of the patient or the like, the mouth-inserting part dissolves in the mouth of the patient or the like and thus falls off, and hence the orally administered agent of the present embodiment can be administered in a shorter time than in the case that the supporting substrate is constituted from an insoluble material that does not dissolve in the mouth.

The orally administered agent and the orally administered agent/supporting substrate complex of the present embodiment can, for example, be manufactured as follows.

A suspension to which a water-swellable gel-forming agent and a film-forming agent have been added (with the solvent being, for example, purified water) is applied, sprayed or the like onto a supporting substrate such as a plastic film or a paper mounting, and then drying is carried out, thus forming a water-swellable gel-forming layer. A suspension to which a drug and additive(s) such as excipient(s), binder(s) and disintegrator(s) have been added (with the solvent being, for example, ethanol) is then applied, sprayed or the like onto the upper surface of the water-swellable gel-forming layer that has been formed, and drying is carried out, thus forming a drug-containing layer. In the case of further forming a water-swellable gel-forming layer on the upper surface of the drug-containing layer, a suspension to which a water-swellable gel-forming agent and a film-forming agent have been added is applied on, sprayed on or the like, and then drying is carried out, as above. In this way, an orally administered agent/supporting substrate complex in which an orally administered agent is supported on the upper surface of a supporting substrate (e.g. an orally administered agent/supporting substrate complex as shown in any of FIGS. 7 to 10) can be manufactured. Moreover, by peeling the supporting substrate off from the orally administered agent/supporting substrate complex, an orally administered agent (e.g. an orally administered agent as shown in any of FIGS. 1 to 5) can be manufactured. If necessary, the orally administered agent/supporting substrate complex and the orally administered agent may be punched out into any desired shape such as a circle, an ellipse or a polygon, and slits may be inserted.

Figure 11:
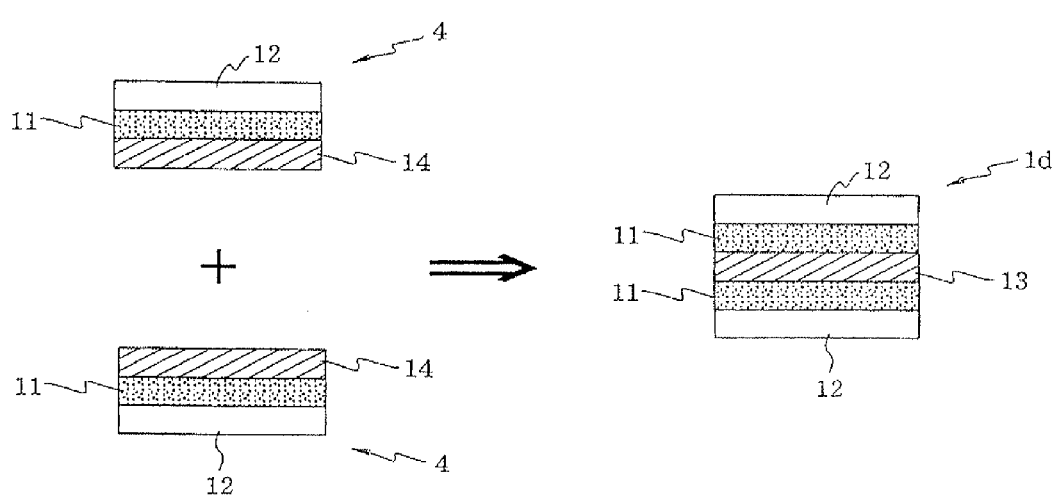
FIG. 11 is a drawing showing an example of a method of manufacturing the orally administered agent of the present invention.

Moreover, after forming a water-swellable gel-forming layer on top of a supporting substrate such as a plastic film or a paper mounting and then forming a drug-containing layer on the upper surface of the water-swellable gel-forming layer as described above, an adhesive layer can be formed on the upper surface of the drug-containing layer by for example applying on or spraying on and then drying a solution containing an adhesive that exhibits adhesiveness upon heating. As a result, a medicinal agent in which a water-swellable gel-forming layer, a drug-containing layer and an adhesive layer have been built up in this order on the upper surface of a supporting substrate (the medicinal agent 4 shown in FIG. 11) can be manufactured. By, for example, thermally fusing together the adhesive layers 14 of medicinal agents 4 that have been manufactured in this way, an orally administered agent 1d in which two drug-containing layers 11 are laminated together via an intermediate layer 13 and water-swellable gel-forming layers 12 are provided as outermost layers (the orally administered agent 1d shown in FIG. 4) can be manufactured. In this case, by supporting one of the medicinal agents 4 that are to be thermally fused together on a supporting substrate in advance, an orally administered agent/supporting substrate complex in which an orally administered agent is supported on the upper surface of a supporting substrate can be manufactured.

Second Embodiment

FIG. 12(a) is a plane view showing the second embodiment of the orally administered pharmaceutical composition of the present embodiment, while FIG. 12(b) is a cross-section (X-X cross-section in FIG. 12(a)) of the same embodiment.

Figure 12:
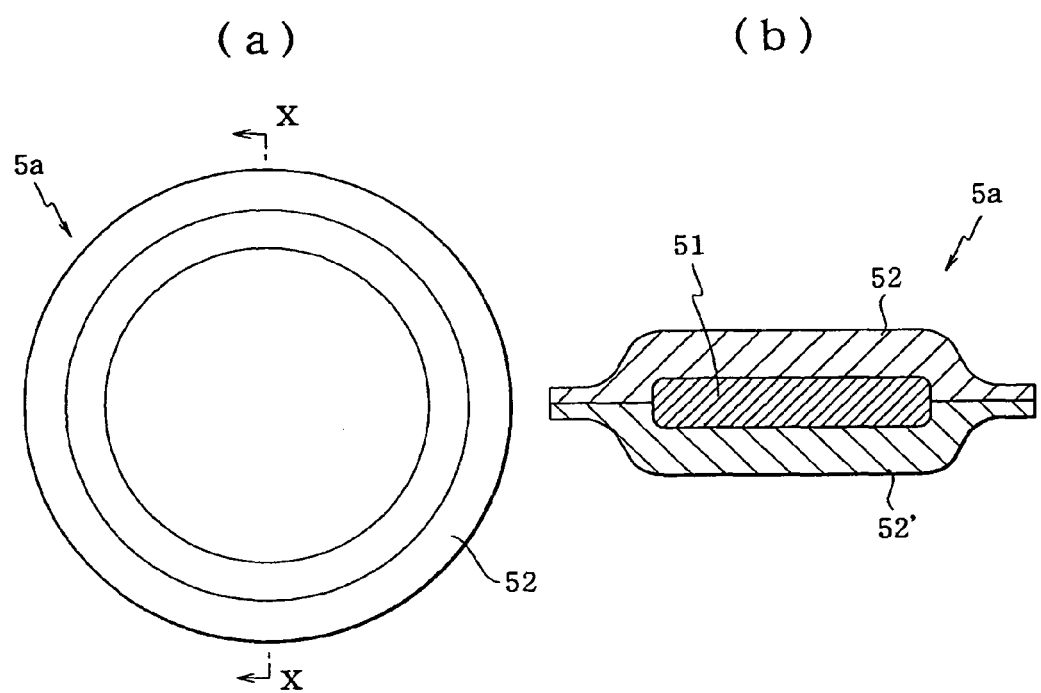
FIG. 12(a) is a plane view showing an embodiment of the orally administered pharmaceutical composition of the present invention.
FIG. 12(b) is a cross-section (X-X cross-section in FIG. 12(a) of the same embodiment.

As shown in FIG. 12, orally administered pharmaceutical composition 5a of the second embodiment comprises water-swellable gel-forming layers 52 and 52' in the outermost layer of orally administered pharmaceutical composition 5a and drug-containing layer 51 layered between water-swellable gel-forming layers 52 and 52', with the outer edge of water-swellable gel-forming layer 52 being bonded directly to the outer edge of water-swellable gel-forming layer 52' so that drug-containing layer 51 is enclosed within orally administered pharmaceutical composition 5a.

As shown in FIG. 12, in orally administered pharmaceutical composition 5a the top and bottom surfaces of drug-containing layer 51 are covered, respectively, by the centers (parts surrounded by outer edges) of water-swellable gel-forming layers 52 and 52', while the sides of drug-containing layer 51 are covered by the bonded outer edges of water-swellable gel-forming layers 52 and 52'. That is, all of drug-containing layer 51 is covered by water-swellable gel-forming layers 52 and 52'. Consequently, when orally administered pharmaceutical composition 5a is administered in the mouth of a patient, water-swellable gel-forming layers 52 and 52' swell from saliva or other moisture to form a gel, and drug-containing layer 51 becomes entirely covered by gel, completely masking the flavor, odor and the like of the drug contained in drug-containing layer 51.

As shown in FIG. 12, water-swellable gel-forming layers 52 and 52' are provided in the outermost layer of orally administered pharmaceutical composition 5a. Consequently, when water-swellable gel-forming layers 52 and 52' gel, orally administered pharmaceutical composition 5a changes to a form of an easy-to-swallow size, shape, elasticity, viscosity and the like. In this way, a patient can easily take orally administered pharmaceutical composition 5a. Since there is also less risk that orally administered pharmaceutical composition 5a will lodge in the patient's trachea during administration, it can be given safely even to elderly patients and infants. In the case of patients who do not have enough saliva to adequately gel water-swellable gel-forming layers 52 and 52', the same effects can be obtained by administering the pharmaceutical composition together with a small amount of water or by soaking it in water before administration. Much less water is required in this case than is required for administering a tablet, capsule or other solid preparation.

Orally administered pharmaceutical composition 5a can be produced for example by the following methods.

[First Production Method]

A suspension containing a water-swellable gel-forming agent and a film-forming agent (with purified water for example as the solvent) is painted, sprayed or otherwise applied to the upper surface of a plastic film, mount or other support base, and dried to form water-swellable gel-forming layer 52, thereby producing a first layered body comprising water-swellable gel-forming layer 52 layered on the upper surface of a support base.

Water-swellable gel-forming layer 52' is formed in the same way on the upper surface of a plastic film, mount or other support base and a suspension containing a drug and excipients, binders, disintegrators and other additives (with ethanol for example as the solvent) is painted, sprayed or otherwise applied to the upper surface of water-swellable gel-forming layer 52' and dried to form drug-containing layer 51. In this case, the size of the bottom surface of drug-containing layer 51 is made smaller than the size of the top surface of water-swellable gel-forming layer 52' (that is, drug-containing layer 51 is formed in the center of the upper surface of water-swellable gel-forming layer 52' so that the outer edges of the upper surface of water-swellable gel-forming layer 52' remain exposed). The method of forming drug-containing layer 51 is not limited to the aforementioned methods, and for example drug-containing layer 51 can be formed on the upper surface of water-swellable gel-forming layer 52' by printing using a known method such as screen printing. In this way, a second layered body is produced comprising water-swellable gel-forming layer 52' and drug-containing layer 51 layered successively on a support base.

Next, the surface of the outer edge of water-swellable gel-forming layer 52 and the surface of the outer edge of water-swellable gel-forming layer 52' are moistened with water to gel them, and the gelled outer edges are pressed together and then dried. In this case, the parts in contact gel and dry as a unit, so that the outer edge of water-swellable gel-forming layer 52 and the outer edge of water-swellable gel-forming layer 52' bond directly to one another. By directly bonding the edge of water-swellable gel-forming layer 52 with the outer edge of water-swellable gel-forming layer 52' in this way, it is possible to produce orally administered pharmaceutical composition 5a comprising drug-containing layer 51 enclosed on the inside.

[Second Production Method]

A first layered body comprising water-swellable gel-forming layer 52 layered on the top surface of a support base and a second layered body comprising water-swellable gel-forming layer 52' layered on the top surface of a support base are produced as in the first production method.

Meanwhile, a suspension containing a drug and excipients, binders, disintegrators and other additives (with ethanol for example as the solvent) is painted, sprayed or otherwise applied to the top surface of a plastic film, mount or other support base, and dried to form a drug-containing film. The drug-containing film thus formed is peeled off the support base, and the resulting drug-containing film is set on the upper surface of water-swellable gel-forming layer 52 of the first layered body or water-swellable gel-forming layer 52' of the second layered body.

Next, the outer edge of water-swellable gel-forming layer 52 of the first layered body and the outer edge of water-swellable gel-forming layer 52' of the second layered body can be bonded directly to one another to produce orally administered pharmaceutical composition 5a comprising a drug-containing film enclosed on the inside.

An orally administered pharmaceutical composition 5a comprising water-swellable gel-forming layer 52', drug-containing layer 51 and water-swellable gel-forming layer 52 layered in that order with drug-containing layer 51 enclosed on the inside can be produced by the aforementioned first or second production method. Orally administered pharmaceutical composition 5a can be punched out in a circular, oval, polygonal or any other shape as necessary. When punching out orally administered pharmaceutical composition 5a, the part where the outer edge of water-swellable gel-forming layer 52 of the first layered body is bonded to the outer edge of water-swellable gel-forming layer 52' of the second layered body is punched so as not to expose drug-containing layer 51.

Third Embodiment

FIG. 13A is a plane view showing the third embodiment of the orally administered pharmaceutical composition of the present invention, while FIG. 13B is a cross-section (X-X cross-section in FIG. 13A) showing the same embodiment.

Figure 13:
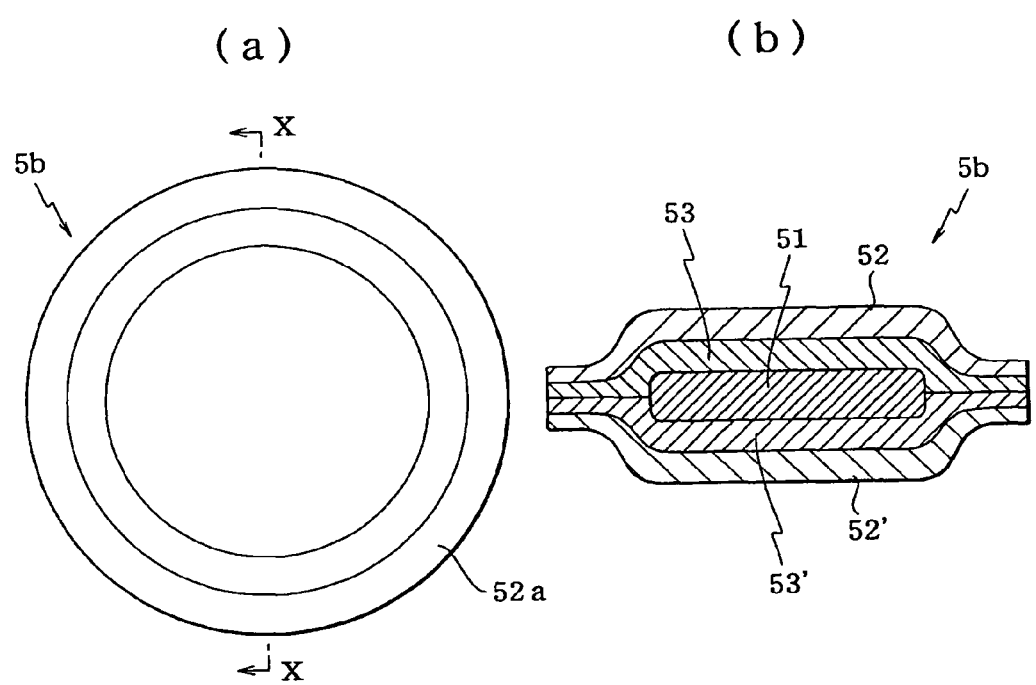
FIG. 13(a) is a plane view showing an embodiment of the orally administered pharmaceutical composition of the present invention.
FIG. 13(b) is a cross-section (X-X cross-section in FIG. 13(a) of the same embodiment.

As shown in FIG. 13, orally administered pharmaceutical composition 5b of the third embodiment comprises water-swellable gel-forming layers 52 and 52' in the outer layer of orally administered pharmaceutical composition 5b, adhesive layer 53 layered on the bottom surface of water-swellable gel-forming layer 52, adhesive layer 53' layered on the top surface of water-swellable gel-forming layer 52', and drug-containing layer 51 layered between water-swellable gel-forming layers 52 and 52' via adhesive layers 53 and 53', with the outer edge of water-swellable gel-forming layer 52 bonded to the outer edge of water-swellable gel-forming layer 52' by means of adhesive layers 53 and 53' so that drug-containing layer 51 is enclosed within orally administered pharmaceutical composition 1. In FIG. 13, the parts that are the same as in FIG. 12 are labeled with the same symbols, and those explanations that are not particularly necessary are omitted.

Orally administered pharmaceutical composition 5b differs from orally administered pharmaceutical composition 5a in terms of the mode of adhesion between the outer edge of water-swellable gel-forming layer 52 and the outer edge of water-swellable gel-forming layer 52', but as in orally administered pharmaceutical composition 5a, drug-containing layer 51 is entirely covered by water-swellable gel-forming layers 52 and 52'. Moreover, water-swellable gel-forming layers 52 and 52' are in the outermost layer as in orally administered pharmaceutical composition 5a. Consequently, the same effects are provided by orally administered pharmaceutical composition 5b as by orally administered pharmaceutical composition 5a.

The adhesive contained in adhesive layers 53 and 53' is not particularly limited as long as it is a pharmacologically acceptable adhesive. Examples of adhesives that exhibit adhesiveness when included in a solvent include carboxyvinyl polymers, sodium polyacrylate and other polyacrylic acids or pharmacologically acceptable non-toxic salts thereof, acrylic acid copolymers or pharmacologically acceptable salts thereof, carboxymethylcellulose, sodium salts and other hydrophilic cellulose derivatives, pullulan, povidone, karaya gum, pectin, xanthan gum, tragacanth, alginic acid, gum arabic, acidic polysaccharides and derivatives and pharmacologically acceptable salts thereof and the like, and 1 or 2 or more of these may be selected and used. Examples of adhesives that exhibit adhesiveness when heated (that is, heat-fusable adhesives) include for example vinyl acetate, polyvinylpyrrolidone and other homopolymers and copolymers of vinyl acetate and vinylpyrrolidone and the like, and 1 or 2 or more of these may be selected and used.

The thickness of adhesive layers 53 and 53' can be adjusted appropriately within a range that allows oral administration, but is preferably 1 to 50 µm or more preferably 10 to 30 µm when orally administered pharmaceutical composition 5b is a film preparation. If adhesive layers 53 and 53' are less than 1 µm thick they may not adhere properly, while if adhesive layers 53 and 53' are more than 50 µm thick they may impede swelling of orally administered adhesive 5b from saliva and the like during administration, and may also make taking the drug unpleasant if the adhesive contained in adhesive layers 53 and 53' is insoluble in water.

Orally administered pharmaceutical composition 5b may be produced for example by the following methods.

[First Production Method]

A suspension containing a water-swellable gel-forming agent and a film-forming agent (with purified water for example as the solvent) is painted, sprayed or otherwise applied to the upper surface of a plastic film, mount or other support base, and dried to form water-swellable gel-forming layer 52. Next, a suspension containing an adhesive (with ethanol for example as the solvent) is painted, sprayed or otherwise applied to the upper surface of water-swellable gel-forming layer 52, and dried to form adhesive layer 53. A first layered body comprising water-swellable gel-forming layer 52 and adhesive layer 53 layered in that order on a support base is produced in this way.

Water-swellable gel-forming layer 52' and adhesive layer 53' are formed successively in the same way. Next, a suspension containing a drug and excipients, binders, disintegrators and other additives (with ethanol for example as the solvent) is painted, sprayed or otherwise applied to the upper surface of adhesive layer 53', and dried to form drug-containing layer 51. In this case, the size of the lower surface of drug-containing layer 51 is made smaller than the size of the upper surface of adhesive layer 53' (that is, drug-containing layer 51 is formed in the center of the upper surface of adhesive layer 53' so that the outer edges of the upper surface of adhesive layer 53' remain exposed). The method of forming drug-containing layer 51 is not confined to the aforementioned method, and for example drug-containing layer 51 can also be formed on the upper surface of adhesive layer 53' by printing using a known method such as screen printing or the like. A second layered body comprising water-swellable gel-forming layer 52', adhesive layer 53' and drug-containing layer 51 layered successively on a support base is produced in this way.

Next, the outer edge of water-swellable gel-forming layer 52 of the first layered body and the outer edge of water-swellable gel-forming layer 52' of the second layered body are bonded together via adhesive layers 53 and 53' to produce orally administered pharmaceutical composition 5b comprising drug-containing layer 51 enclosed on the inside. In this case, the desired mode of adhesion can be selected by selecting the adhesive contained in adhesive layers 53 and 53'. When adhesive layers 53 and 53' contain a heat-fusable adhesive, they can be bonded by heat fusion. Heat fusion can be performed at a temperature of normally 60 to 150° C. or preferably 90 to 120° C. under normally at least 0.1 kgf/cm$^2$ preferably at least 0.5 kgf/cm$^2$ for normally 0.1 to 5 seconds or preferably 0.5 to 3 seconds.

[Second Production Method]

A first layered body comprising water-swellable gel-forming layer 52 and adhesive layer 53 layered successively on a support base and a second layered body comprising water-swellable gel-forming layer 52' and adhesive layer 53' layered successively on a support base are produced as in first production method.

Meanwhile, a suspension containing a drug and excipients, binders, disintegrators and other additives (with ethanol for example as the solvent) is painted, sprayed or otherwise applied to the upper surface of a plastic film, mount or other support member, and dried to form drug-containing layer 51. The resulting drug-containing layer 51 is peeled from the support member to obtain a drug-containing film which is the set on adhesive layer 53 of the first layered body or adhesive layer 53' of the second layered body.

Next, the outer edge of adhesive layer 53 of the first layered body can be bonded to the outer edge of adhesive layer 53' of the second layered body as described above to produce orally administered pharmaceutical composition 5b comprising a drug-containing film enclosed on the inside.

Orally administered pharmaceutical composition 5b comprising water-swellable gel-forming layer 52', adhesive layer 53', drug-containing layer 51, adhesive layer 53 and water-swellable gel-forming layer 52 layered in that order with drug-containing layer 51 enclosed on the inside is produced by the aforementioned first or second production method. Orally administered pharmaceutical composition 5b may also be punched out in a round, oval or polygonal shape or in any other shape as necessary. When punching out orally administered pharmaceutical composition 5b, the part where the outer edge of water-swellable gel-forming layer 52 of the first layered body is bonded to the outer edge of water-swellable gel-forming layer 52' of the second layered body is punched so as not to expose drug-containing layer 51.

The following alterations are possible in orally administered pharmaceutical compositions 5a and 5b.

Orally administered pharmaceutical compositions 5a and 5b may have functional layers other than water-swellable gel-forming layers and adhesive layers. An example of such a functional layer is a layer for purposes of adjusting film thickness. When orally administered pharmaceutical compositions 5a and 5b are film preparations, orally administered pharmaceutical compositions 5a and 5b can be made easier to handle by using such a layer to increase the film thickness. Such a functional layer is provided between water-swellable gel-forming layers 52 and 52'.

Orally administered pharmaceutical compositions 5a and 5b each have 1 drug-containing layer, but the number of drug-containing layers is not particularly limited, and orally administered pharmaceutical compositions 5a and 5b may have multiple drug-containing layers. When orally administered pharmaceutical compositions 5a and 5b have multiple drug-containing layers, the drug-containing layers may be layered directly or via an intermediate layer. Moreover, one drug-containing layer may be constituted by multiple drug-containing layers formed side by side.

Orally administered pharmaceutical compositions 5a and 5b each have 2 water-swellable gel-forming layers, but they may also have another water-swellable gel-forming layer. Such a water-swellable gel-forming layer may be provided between water-swellable gel-forming layer 52 and water-swellable gel-forming layer 52', or may be provided outside water-swellable gel-forming layers 52 and 52'.

A drug-containing layer is enclosed inside orally administered pharmaceutical compositions 5a and 5b, but a drug that does not form a drug-containing layer could also be enclosed. For example, a drug formulated in a tablet, powder or other appropriate form could be enclosed without forming a drug-containing layer. A drug can be easily enclosed inside orally administered pharmaceutical compositions 5a and 5b using a formulated drug (see second production method above). By enclosing an already formulated drug in orally administered pharmaceutical compositions 5a and 5b it is possible to limit the amount of excess drug used during the production of orally administered pharmaceutical compositions 5a and 5b, thereby reducing costs.

Figure 14:
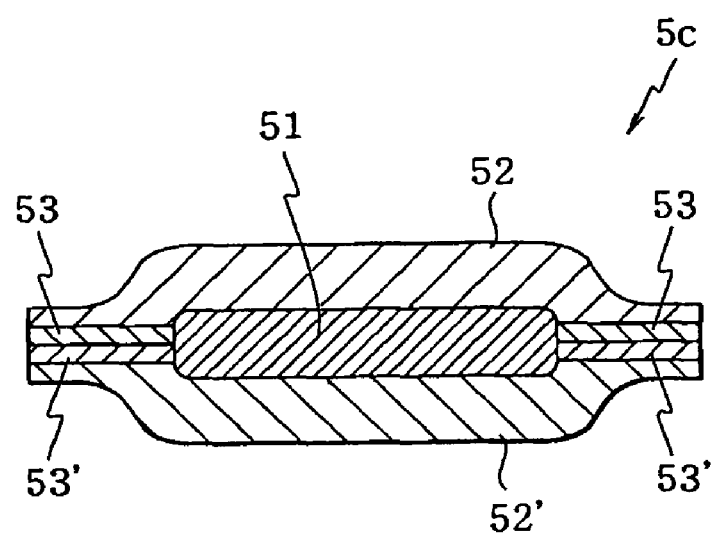
FIG. 14 is a cross-section showing another embodiment of the orally administered pharmaceutical composition of the present invention.

In orally administered pharmaceutical composition 5b adhesive layers 53 and 53' are layered over the entire lower surface of water-swellable gel-forming layer 52 and the entire upper surface of water-swellable gel-forming layer 52', respectively, but the sizes and positions of adhesive layers 53 and 53' are not particularly limited as long as they allow the outer edge of water-swellable gel-forming layer 52 to be bonded to the outer edge of water-swellable gel-forming layer 52'. For example, adhesive layers 53 and 53' may be layered on one part (the outer edge) of the lower surface of water-swellable gel-forming layer 52 and one part (the outer edge) of the upper surface of water-swellable gel-forming layer 52', respectively, as in orally administered pharmaceutical composition 5c shown in FIG. 14.

Figure 15:
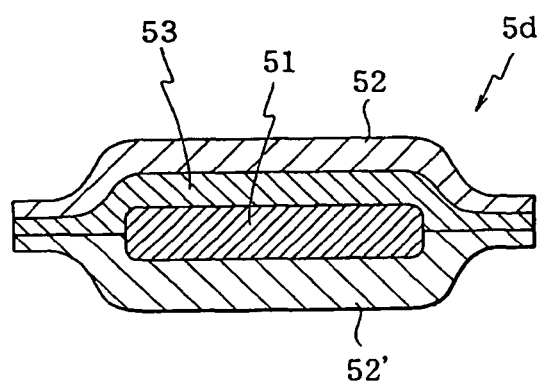
FIG. 15 is a cross-section showing yet another embodiment of the orally administered pharmaceutical composition of the present invention.
Figure 15:
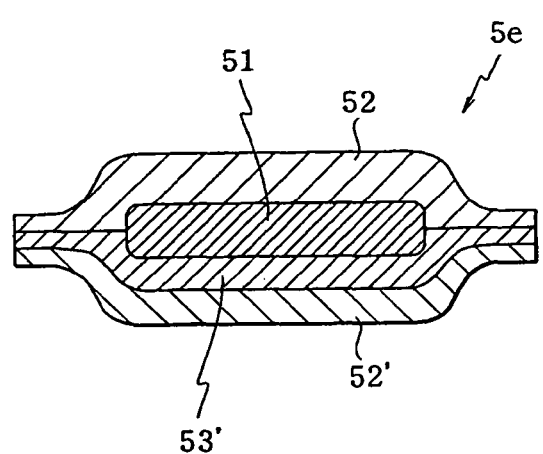
Figure 15:
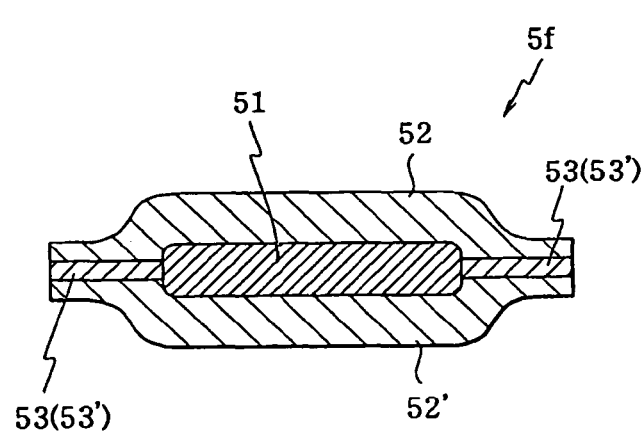

Orally administered pharmaceutical composition 5b comprises two adhesive layers 53 and 53' between the outer edge of water-swellable gel-forming layer 52 and the outer edge of water-swellable gel-forming layer 52', but the number of adhesive layers provided between the outer edge of water-swellable gel-forming layer 52 and the outer edge of water-swellable gel-forming layer 52' is not particularly limited as long as it allows the outer edge of water-swellable gel-forming layer 52 to be bonded to the outer edge of water-swellable gel-forming layer 52'. For example, there may be only 1 adhesive layer between the outer edge of water-swellable gel-forming layer 52 and the outer edge of water-swellable gel-forming layer 52' as in orally administered pharmaceutical compositions 5d through 5f shown in FIGS. 15A through 15C.

In the orally administered pharmaceutical composition of the present embodiment, the drug contained inside the orally administered pharmaceutical composition is completely covered by the first and second water-swellable gel-forming layers. Consequently, when the orally administered pharmaceutical composition of the present embodiment is administered in the mouth of a patient, the first and second water-swellable gel-forming layers swell from saliva or other moisture to form a gel, so that the entire drug contained inside the orally administered pharmaceutical composition becomes covered by gel, completely masking the flavor, odor and the like of the drug.

The drug may be enclosed inside the orally administered pharmaceutical composition in any state in the orally administered pharmaceutical composition of the present embodiment. For example, the drug may be enclosed inside the orally administered pharmaceutical composition in a drug-containing layer or in the form of a tablet, powder, liquid or other appropriate preparation. One mode of the orally administered pharmaceutical composition of the present embodiment comprises a drug-containing layer provided between the aforementioned first water-swellable gel-forming layer and second water-swellable gel-forming layer, with the outer edges of the first water-swellable gel-forming layer and second water-swellable gel-forming layer bonded together so that the drug-containing layer is completely enclosed inside the orally-administered pharmaceutical composition.

In the orally administered pharmaceutical composition of the present embodiment, there are no limits on how the outer edge of the first water-swellable gel-forming layer is bonded to the outer edge of the second water-swellable gel-forming layer as long as the drug is enclosed within the orally administered pharmaceutical composition, and the outer edge of the first water-swellable gel-forming layer and the outer edge of the second water-swellable gel-forming layer may be bonded directly or may be bonded via an adhesive layer.

Following is a more detailed description of the present invention through manufacturing examples and test examples.

Examples for the First Embodiment

Manufacturing Examples 1

Manufacture of Orally Administered Agents and Orally Administered Agent/Supporting Substrate Complexes (1) Manufacture of Stomach-Soluble Preparation and Stomach-Soluble Preparation/Supporting Substrate Complex A liquid A of the composition shown in Table 1 below was prepared for forming water-swellable gel-forming layers. That is, 45 g of purified water was taken, and 10.5 g of polyvinyl alcohol (Gohsenol EG05T (Nippon Synthetic Chemical Industry Co., Ltd.)) was added thereto slowly with stirring, and was then dissolved completely by stirring for about 1 hour while heating to 70° C. Similarly, 40 g of purified water was taken, and 4.05 g of polyacrylic acid (Junlon PW-111 (Nihon Junyaku Co., Ltd.)) was added thereto slowly with stirring, and was then dissolved completely by stirring for about 30 minutes. These two solutions were combined and thorough stirring was carried out, and then 0.45 g of calcium chloride was added, and stirring was carried out for a further 5 minutes. Note that the polyacrylic acid is cross-linked by calcium ions that are generated through the calcium chloride undergoing electrolytic dissociation, and the cross-linked polyacrylic acid fulfils the role of a water-swellable gel-forming agent, while the polyvinyl alcohol fulfils the role of a film-forming agent.

TABLE 1

| Liquid A | |
|---|---|
| Polyvinyl alcohol | 10.5 g |
| Polyacrylic acid | 4.05 g |
| Calcium chloride | 0.45 g |
| Purified water | 85.0 g |

A liquid B of the composition shown in Table 2 below was prepared for forming a drug-containing layer. That is, 70 g of ethanol was taken, and 22.5 g of hydroxypropyl cellulose (Nisso HPC (SL grade), Nippon Soda Co., Ltd.) was added thereto slowly with stirring, and was then dissolved completely by stirring for about 30 minutes. Next, 7.5 g of famotidine, which is a gastric ulcer drug, was added, and stirring was carried out for about a further 5 minutes.

TABLE 2

| Liquid B | |
|---|---|
| Famotidine | 7.5 g |
| Hydroxypropyl cellulose | 22.5 g |
| Ethanol | 70.0 g |

The liquid A was degassed, and then this solution was applied onto a surface of a 38 μm-thick polyethylene terephthalate film (hereinafter referred to as 'PET film') onto which a silicone resin releasing agent had been applied, and drying was carried out for about 10 minutes at 80° C., thus forming a water-swellable gel-forming layer of thickness about 50 μm. Next, the liquid B was degassed, and then this solution was applied onto the water-swellable gel-forming layer, and drying was carried out for about 5 minutes at 80° C., thus forming a drug-containing layer of thickness about 70 μm. The liquid A was then further applied onto the drug-containing layer, and drying was carried out for about 10 minutes at 80° C., thus forming a water-swellable gel-forming layer of thickness about 50 μm. In this way, an orally administered agent/supporting substrate complex in which an orally administered agent (film-shaped preparation comprising three layers, i.e. a water-swellable gel-forming layer, a drug-containing layer, and a water-swellable gel-forming layer) is supported on the above-mentioned PET film as a supporting substrate was manufactured (see FIG. 8). The orally administered agent was punched out to a diameter of 30 mm, and in the undermentioned tests the orally administered agent was used after being peeled off from the PET film.

(2) Manufacture of Intestine-Soluble Preparation and Intestine-Soluble Preparation/Supporting Substrate Complex The liquid A of the composition shown in Table 1 above was prepared as described above for forming water-swellable gel-forming layers.

A liquid C of the composition shown in Table 3 below was prepared for forming a drug-containing layer. That is, 35 g of each of acetone and ethanol were taken, and 22.5 g of hydroxypropyl methyl cellulose phthalate (Kanto Kagaku) was added thereto slowly with stirring, and was then dissolved completely by stirring for about 30 minutes. Next, 7.5 g of the above-mentioned famotidine was added, and stirring was carried out for about a further 5 minutes.

TABLE 3

| Liquid C | |
|---|---|
| Famotidine | 7.5 g |
| Hydroxypropyl methyl cellulose phthalate | 22.5 g |
| Acetone | 35.0 g |
| Ethanol | 35.0 g |

The liquid A was degassed, and then this solution was applied onto a surface of a 38 μm-thick polyethylene terephthalate film (hereinafter referred to as 'PET film') onto which a silicone resin releasing agent had been applied, and drying was carried out for about 10 minutes at 80° C., thus forming a water-swellable gel-forming layer of thickness about 50 μm. Next, the liquid C was degassed, and then this solution was applied onto the water-swellable gel-forming layer, and drying was carried out for about 5 minutes at 70° C., thus forming a drug-containing layer of thickness about 70 μm. The liquid A was then further applied onto the drug-containing layer, and drying was carried out for about 10 minutes at 80° C., thus forming a water-swellable gel-forming layer of thickness about 50 μm. In this way, an orally administered agent/supporting substrate complex in which an orally administered agent (film-shaped preparation comprising three layers, i.e. a water-swellable gel-forming layer, a drug-containing layer, and a water-swellable gel-forming layer) is supported on the above-mentioned PET film as a supporting substrate was manufactured (see FIG. 8). The orally administered agent was punched out to a diameter of 30 mm, and in the undermentioned tests the orally administered agent was used after being peeled off from the PET film.

(3) Manufacture of Orally Administered Agent/Supporting Substrate Complex Suitable for Oral Administration In (1) and (2) above, a PET film of length 100 mm, width 25 mm and thickness 38 μm was used as the supporting substrate, thus manufacturing an orally administered agent/supporting substrate complex as in FIG. 10. This supporting substrate has a part that can be grasped in the hand (gripping part) (length 30 mm) and a part that can be inserted into the mouth of a patient or the like (mouth-inserting part) (length 70 mm), and the orally administered agent is provided on the mouth-inserting part.

Test Example 1

Evaluation Tests into Ease and Safety of Taking Agent, and Masking of Taste of Drug Ten randomly sampled test subjects 10 were asked to take without water the orally administered agents manufactured in manufacturing examples 1 (stomach-soluble preparation and intestine-soluble preparation), and the ease of taking the agent and the drug taste masking ability were evaluated in accordance with the 5-level evaluation criteria described below. Moreover, at the same time evaluation was also carried out into whether or not the agent got stuck in the throat, airway or esophagus when taken (i.e. the safety of taking the agent)

[Evaluation Criteria for Ease of Taking Agent]
1: Doesn't swell and gelate, cannot be taken without water.
2: Swells and gelates slightly, but cannot be taken without water.
3: Swells and gelates, but would like to take with water if possible.
4: Swells and gelates slowly, and can be taken without water.
5: Swells and gelates rapidly, and can be taken without water.

[Evaluation Criteria for Masking Ability]
1: Taste of drug spreads through mouth as soon as put into mouth, problems with taking.
2: No taste immediately after putting into mouth, but taste appears before swallowing, and hence problems with taking.
3: Taste of drug sensed while in mouth, but to extent that no problems with taking.
4: Taste of drug hardly sensed.
5: No taste of drug whatsoever.

The results for the stomach-soluble preparation are shown in Table 4 below, and the results for the intestine-soluble preparation are shown in Table 5 below.

TABLE 4

| | Test subject | | | | | | | | | | |
|---|---|---|---|---|---|---|---|---|---|---|---|
| Evaluation item | 1 | 2 | 3 | 4 | 5 | 6 | 7 | 8 | 9 | 10 | Mean |
| Ease of taking | 5 | 5 | 5 | 5 | 4 | 5 | 5 | 5 | 5 | 5 | 4.9 |
| Masking ability | 5 | 5 | 5 | 5 | 4 | 5 | 4 | 5 | 5 | 5 | 4.8 |
| Sticks in throat etc. | No | No | No | No | No | No | No | No | No | No | |

TABLE 5

| | Test subject | | | | | | | | | | |
|---|---|---|---|---|---|---|---|---|---|---|---|
| Evaluation item | 1 | 2 | 3 | 4 | 5 | 6 | 7 | 8 | 9 | 10 | Mean |
| Ease of taking | 5 | 5 | 5 | 5 | 4 | 5 | 5 | 5 | 5 | 5 | 4.9 |
| Masking ability | 5 | 5 | 5 | 5 | 5 | 5 | 5 | 5 | 5 | 5 | 5.0 |
| Sticks in throat etc. | No | No | No | No | No | No | No | No | No | No | |

As shown in Tables 4 and 5, the orally administered agents (stomach-soluble preparation and intestine-soluble preparation) manufactured in manufacturing examples 1 were excellent in terms of ease and safety of taking the agent, and masking of the taste of the drug.

Test Example 2

Evaluation Tests into Film Strength

An orally administered agent that was a film-shaped preparation (stomach-soluble preparation or intestine-soluble preparation) was manufactured as in manufacturing example 1 (1) or (2), and the film strength for the case that the drug content in the drug-containing layer was changed was measured in accordance with a JIS tensile strength test (JIS Z0237). The composition and thickness of the water-swellable gel-forming layer in the film-shaped preparation were made to be the same conditions as in manufacturing example 1 (1) or (2), but the number of water-swellable gel-forming layers was made to be one. Moreover, the drug content in the drug-containing layer was changed between 0.1 wt %, 10 wt %, 25 wt %, 50 wt %, and 80 wt %.

The results of the film strength ($kg/cm^2$) for the stomach-soluble preparation and the intestine-soluble preparation are shown in Table 6 below.

TABLE 6

| | Drug content (wt %) | | | | |
|---|---|---|---|---|---|
| | 0.1 | 10 | 25 | 50 | 80 |
| Stomach-soluble preparation | 583 | 572 | 551 | 538 | 520 |
| Intestine-soluble preparation | 575 | 570 | 559 | 530 | 511 |

As shown in Table 6, in the film-shaped preparations manufactured in manufacturing example 1, a sufficient film strength could be maintained even when the drug content (wt %) in the drug-containing layer was changed over a broad range of 0.1 to 80 wt %.

Test Example 3

Evaluation Tests into Ease of Administration Using Orally Administered Agent/Supporting Substrate Complex, and Ease of Checking Whether Agent has been Taken An orally administered agent supported in an orally administered agent/supporting substrate complex manufactured as in manufacturing example 1 (3) was administered without water to ten randomly sampled test subjects who were lying down, and the ease of administration and the ease of checking whether the agent has been taken were evaluated in accordance with the following evaluation criteria.

[Evaluation Criteria for Ease of Administration]
1: Hand gets soiled, administration difficult.
2: Sometimes get hand soiled, but administration possible.
3: Don't get hand soiled at all, can administer easily.

[Evaluation Criteria for Ease of Checking Whether Agent has Been Taken]
1: Cannot check at all.
2: Checking difficult, but can check whether or not taking of agent has been completed.
3: Can check at a glance whether or not taking of agent has been completed.

The results of the evaluation tests are shown in Table 7 below.

TABLE 7

| | Test subject | | | | | | | | | | |
|---|---|---|---|---|---|---|---|---|---|---|---|
| Evaluation item | 1 | 2 | 3 | 4 | 5 | 6 | 7 | 8 | 9 | 10 | Mean |
| Ease of administration | 3 | 3 | 3 | 3 | 3 | 3 | 3 | 3 | 3 | 3 | 3.0 |
| Ease of checking | 3 | 3 | 3 | 3 | 3 | 3 | 3 | 3 | 3 | 3 | 3.0 |

As shown in Table 7, the orally administered agent supported in an orally administered agent/supporting substrate complex gelated within 5 minutes inside the mouth of a test subject, and hence the orally administered agent could easily be administered even if the test subject was lying down. Moreover, by taking the supporting substrate on which the orally administered agent was supported out of the mouth of the test subject, it could easily be checked whether or not taking of the agent had been completed. Moreover, during the sequence of operations from administration to checking whether the agent had been taken, there was no soiling whatsoever of the hand or fingers by the test subject's saliva or the like. Moreover, in the case that the amount of secretion of saliva is low as with an elderly person or the like, one would think that it is necessary to dip the film-shaped preparation in water before administration, but by using the orally administered agent/supporting substrate complex, this dipping in water could also be carried out easily.

Test Example 4

Study into Mixing Proportions of Water-Swellable Gel-Forming Agent, Film-Forming Agent and Cross-Linking Agent in Water-Swellable Gel-Forming Layers The mixing proportions (wt %) of the water-swellable gel-forming agent, the film-forming agent and the cross-linking agent in the water-swellable gel-forming layers were changed, and the solubility and the swellability of the film-shaped preparations when actually in the mouth were evaluated using the senses. The film-shaped preparations were manufactured in accordance with manufacturing example 1 (1); the composition of the drug-containing layer was set to be as in manufacturing example 1 (1), and the composition of the water-swellable gel-forming layers was set as in Table 8 below (the units are wt %).

TABLE 8

|  | film-forming agent: Polyvinyl alcohol | water-swellable gel-forming agent: Polyacrylic acid | cross-linking agent: Calcium chloride |
|---|---|---|---|
| Comparative example 1 | 100.0 | 0 | 0 |
| Comparative example 2 | 95.0 | 5.0 | 0 |
| Comparative example 3 | 85.0 | 15.0 | 0 |
| Comparative example 4 | 95.0 | 4.5 | 0.5 |
| Example 1 | 70.0 | 27.0 | 3.0 |
| Example 2 | 44.4 | 50.0 | 5.6 |
| Example 3 | 85.0 | 13.5 | 1.5 |

The results of the test are shown in Table 9 below.

TABLE 9

|  | Evaluation |
|---|---|
| Comparative example 1 | Δ: Dissolves slowly. Doesn't gelate, becomes highly viscous solution. Masking insufficient. |
| Comparative example 2 | X: Dissolves rapidly. Doesn't gelate. Masking insufficient. |
| Comparative example 3 | X: Dissolves rapidly. Doesn't gelate. Masking insufficient. |
| Comparative example 4 | Δ: Gelates to some extent. Masking insufficient. |
| Example 1 | ⊚: Gelation sufficient. Masking sufficient. |
| Example 2 | ⊙: Gelation sufficient. Masking sufficient. |
| Example 3 | ○: Gelation almost sufficient. Masking almost sufficient. |

Examples for the Second and Third Embodiments (1) Preparation of Water-Swellable Gel-Forming Layer Forming Liquid (Coating Liquid A)

Coating liquid A was prepared with the following composition for purposes of forming the water-swellable gel-forming layers. 1 g of potassium alum was added to 140 g of purified water, and completely dissolved by agitation for about 10 minutes. Next, 6 g of polyacrylic acid (Carbopol 974P. BF Goodrich) was added gradually with agitation, and completely dissolved by being agitated for about 1 hour. Next, 17 g of polyvinyl alcohol (Gohsenol EG-05T, Nippon Gohsei) was added gradually with agitation, and completely dissolved by agitation with heating at 70° C. for about 1 hour.

Polyacrylic acid is crosslinked by the aluminum ions produced by ionization of potassium alum, and the crosslinked polyacrylic acid serves as a water-swellable gel-forming agent, while the polyvinyl alcohol serves as a film-forming agent.

(2) Preparation of Adhesive Layer Forming Liquid (Coating Liquid B)

Coating Liquid B was prepared with the following composition for purposes of forming the adhesive layer. That is, 6 g of polyvinylpyrrolidone (PVP K-90, ISP Japan) was added gradually with agitation to 25 g of ethanol, and 1 g of glycerin was then added and completely dissolved by agitation for about 20 minutes. Polyvinylpyrrolidone is heat-fusable because it is a thermoplastic polymer.

(3) Preparation of Drug-Containing Layer Forming Liquid (Coating Liquid C)

Coating liquid C was prepared with the following composition for purposes of forming the drug-containing layer. That is, 7 g of the stomach ulcer drug famotidine and 0.2 g of titanium oxide were added to ethanol or purified water and thoroughly dispersed with a homogenizer, after which 20 g of any of the bases (binders) listed under (a) through (k) below was added and completely dissolved by being agitated for about 20 minutes:

(a) Polyvinylpyrrolidone (PVP K-30, ISP Japan)
(b) Polyvinylpyrrolidone-vinyl acetate copolymer (S-630, ISP Japan)
(c) Carboxymethyl cellulose sodium (Kanto Chemical Co., Inc.)
(d) Hydroxypropyl cellulose (HPC SL Grade, Nippon Soda)
(e) Gum arabic
(f) Guar gum
(g) Xanthan gum
(h) Gum tragacanth
(i) Locust bean gum
(j) Carageenan
(k) Sodium alginate.

The amount of the solvent was adjusted appropriately so as to achieve a viscosity of 2000 to 6000 mPa·s.

Production Example 2

Production of Orally Administered Pharmaceutical Composition A (1) Formation of Water-Swellable Gel-Forming Layer Coating Liquid A was thoroughly degassed and, using an applicator with the gap adjusted so as to achieve a thickness of 30 μm after drying, spread on the opposite side of a polyethylene terephthalate film (Lintec Corporation, SP-PET3801) which had been release-treated on one side with a silicone resin, and dried for 10 minutes at 80° C. to form a water-swellable gel-forming layer. Layered body A was thus produced comprising a water-swellable gel-forming layer layered on the aforementioned polyethylene terephthalate film. Another layered body A was produced in the same way.

(2) Formation of Drug-Containing Layer

Coating Liquid C was thoroughly degassed and 100 μL was dripped onto the top surface of the water-swellable gel-forming layer of a layered body A and dried for about 15 minutes at 80° C. to form a drug-containing layer. The drug-containing layer in this case was formed not on the entire top surface of the water-swellable gel-forming layer but only on part of the top surface. That is, the drug-containing layer was layered on the center (area about 1.8 cm$^2$) of the top surface (area about 4.9 cm$^2$) of the water-swellable gel-forming layer so as not to cover the outer edges of the water-swellable gel-forming layer. In this way, a layered body B was produced comprising a water-swellable gel-forming layer and drug-containing layer layered successively on the aforementioned polyethylene terephthalate film.

(3) Production of Orally Administered Pharmaceutical Composition by Direct Adhesion of Water-Swellable Gel-Forming Layers Purified water was applied to gel the surface of the outer edge of the water-swellable gel-forming layer of layered body A and the surface of the outer edge of the water-swellable gel-forming layer of layered body B, the gelled outer edges were pressed together, one of the polyethylene terephthalate films was peeled off, and the whole was dried for about 5 minutes at 80° C. to directly bond the outer edge of the water-swellable gel-forming layer of layered body A with the outer edge of the water-swellable gel-forming layer of layered body B. In this way, a layered body was produced comprising a water-swellable gel-forming layer, drug-containing layer and water-swellable gel-forming layer layered successively on the aforementioned polyethylene terephthalate film with the drug-containing layer enclosed on the inside, and this layered body was punched out to produce orally administered pharmaceutical composition A. When punching out the layered body, the part where the water-swellable gel-forming layers were bonded to one another was punched so as not to expose the drug-containing layer.

Production Example 3

Production of Orally Administered Pharmaceutical Composition B (1) Formation of Water-Swellable Gel-Forming Layer Coating Liquid A was thoroughly degassed and, using an applicator with the gap adjusted so as to obtain a dried thickness of 30 μm, spread on the opposite side of a polyethylene terephthalate film (Lintec Corporation, SP-PET3801) which had been release-treated on one side with a silicone resin, and dried for 10 minutes at 80° C. to form a water-swellable gel-forming layer.

(2) Formation of Adhesive Layer

Coating Liquid B was thoroughly degassed and, using an applicator with the gap adjusted so as to obtain a dried thickness of 20 μm, spread on the entire top surface of the aforementioned water-swellable gel-forming layer, and dried for about 3 minutes at 80° C. to form an adhesive layer. In this way, layered body C was produced comprising a water-swellable gel-forming layer and adhesive layer layered in that order on the aforementioned polyethylene terephthalate film. Another layered body C was produced in the same way.

(3) Formation of Drug-Containing Layer

Coating Liquid C was thoroughly degassed, and 100 μL was dripped onto the top surface of the adhesive layer of layered body C and dried for about 15 minutes at 80° C. to form a drug-containing layer. In this case, the drug-containing layer was formed on only part of the top surface, not on the entire top surface of the adhesive layer. That is, the drug-containing layer was formed in the center (area about 1.8 cm$^2$) of the top surface (area about 4.9 cm$^2$) of the adhesive layer so as not to cover the outer edges of the adhesive layer. In this way, a layered body D was produced comprising a water-swellable gel-forming layer, an adhesive layer and a drug-containing layer layered in that order on the aforementioned polyethylene terephthalate film.

(4) Production of Orally Administered Pharmaceutical Composition by Heat Fusion of Adhesive Layers The outer edge of the adhesive layer of layered body C and the outer edge of the adhesive layer of layered body D were heat fused together under conditions of 100° C., 1 kgf/cm$^2$, 2 seconds. In this way, a layered body was produced comprising a water-swellable gel-forming layer, adhesive layer, drug-containing layer, adhesive layer and water-swellable gel-forming layer layered in that order on the aforementioned polyethylene terephthalate film, and this layered body was punched out to produce orally administered pharmaceutical composition B. When punching out this layered body, the part where the adhesive layers had been heat fused to each other was punched out so as not to expose the drug-containing layer.

Production Example 4

Production of Orally Administered Pharmaceutical Compositions C Through F (1) Production of Orally Administered Pharmaceutical Composition C 7 g of the stomach ulcer drug famotidine and 0.2 g of titanium oxide were added to ethanol and thoroughly dispersed with a homogenizer, after which 20 g of polyvinylpyrrolidone (PVP K-90, ISP Japan) was added gradually with agitation and thoroughly dissolved by being agitated for about 20 minutes. The amount of solvent was adjusted appropriately so as to achieve a viscosity of 2000 to 6000 mPa·s.

The resulting coating liquid was thoroughly degassed and, using an applicator with the gap adjusted so as to obtain a dried thickness of 70 μm, spread on the opposite side of a polyethylene terephthalate film (Lintec Corporation, SP-PET3801) which had been release treated on one side with silicone resin, and dried for about 15 minutes at 80° C. to form the drug-containing layer. Next, the drug-containing layer was peeled of the polyethylene terephthalate film to obtain a drug-containing film.

This drug-containing film was set on the adhesive layer of layered body C, and the outer edge of the adhesive layer of this layered body C and the outer edge of the adhesive layer of another layered body C were heat fused together under conditions of 100° C., 1 kgf/cm$^2$, 2 seconds. The drug-containing film was set in the middle (area about 1.8 cm$^2$) of the top surface (area about 4.9 cm$^2$) of the adhesive layer. In this way, a layered body was produced comprising a water-swellable gel-forming layer, adhesive layer, drug-containing film, adhesive layer and water-swellable gel-forming layer layered in that order on the aforementioned polyethylene terephthalate film, with the drug-containing film enclosed inside the layered body, and this layered body was punched out to produce orally administered pharmaceutical composition C. When punching out the layered body, the part where the adhesive layers had been heat-fused together was punched out so as not to expose the drug-containing film.

(2) Production of Orally Administered Pharmaceutical Composition D

Using a 60 mesh (140 μm wire) screen with a 15 mm φ block formed thereon, the coating liquid prepared in (1) above was screen printed on the center (area about 1.8 cm²) of the top surface (area about 4.9 cm²) of the adhesive layer of a layered body C, and dried for about 15 minutes at 80° C. This was repeated until the dried thickness was 70 μm to form a drug-containing layer. In this way, layered body E was produced comprising a water-swellable gel-forming layer, adhesive layer and drug-containing layer layered successively on the aforementioned polyethylene terephthalate film. The outer edge of the adhesive layer of a layered body C and the outer edge of the adhesive layer of layered body E were heat fused together under conditions of 100° C., 1 kgf/cm², 2 seconds. In this way, a layered body was produced comprising a water-swellable gel-forming layer, an adhesive layer, a drug-containing layer, an adhesive layer and a water-swellable gel-forming layer layered in that order on the aforementioned polyethylene terephthalate film with the drug-containing layer enclosed on the inside, and this layered body was punched out to produce orally administered pharmaceutical composition D. When punching out the layered body, the part where the adhesive layers had been heat-fused together was punched out so as not to expose the drug-containing film.

(3) Production of Orally Administered Pharmaceutical Composition E 500 mg of powder obtained by thoroughly mixing famotidine and lactose (excipient) in proportions of 1:49 by weight in a mortar was sprinkled on the top surface of the adhesive layer of layered body C, and the outer edge of the adhesive layer of this layered body C was heat fused with the outer edge of the adhesive layer of another layered body C under conditions of 100° C., 1 kgf/cm², 2 seconds. In this way, a layered body was produced comprising a water-swellable gel-forming layer, an adhesive layer, a drug powder, an adhesive layer and a water-swellable gel-forming layer layered in that order on the aforementioned polyethylene terephthalate film with the drug powder enclosed on the inside, and this layered body was punched out to produce orally administered pharmaceutical composition E. When punching out the layered body, the part where the adhesive layers had been heat-fused together was punched out so as not to expose the drug powder.

(4) Production of Orally Administered Pharmaceutical Composition F

A mixed powder of famotidine and polyvinylpyrrolidone (PVP K-90, ISP Japan) in proportions of 1:49 by weight was tablet molded with a tableting machine using the KBr method. The resulting tablet was set on the upper surface of the adhesive layer of a layered body C, and the outer edge of the adhesive layer of this layered body C was heat fused with the outer edge of the adhesive layer of another layered body C under conditions of 100° C., 1 kgf/cm², 2 seconds. In this way, a layered body was produced comprising a water-swellable gel-forming layer, an adhesive layer, a tablet, an adhesive layer and a water-swellable gel-forming layer layered in that order on the aforementioned polyethylene terephthalate film, and this layered body was punched out to produce orally administered pharmaceutical composition F. When punching out the layered body, the part where the adhesive layers had been heat-fused together was punched out so as not to expose the tablet.

Test Example 5

Test to Evaluate Masking of Drug Flavor

The orally administered pharmaceutical composition A produced in Production Example 2 and the orally administered pharmaceutical composition B produced in Production Example 3 were given with water to 10 randomly selected test subjects, and the ability to mask the flavor of the drug was evaluated according to the following 3-point scale. The results for orally administered pharmaceutical composition A are shown in Table 10, and the results for orally administered pharmaceutical composition B in Table 11.

[Evaluation of Masking]

1 Drug flavor detected

2 Slight drug flavor detected

3 No drug flavor detected

TABLE 10

| Type of base in drug-containing layer | Test subject | | | | | | | | | | |
|---|---|---|---|---|---|---|---|---|---|---|---|
| | 1 | 2 | 3 | 4 | 5 | 6 | 7 | 8 | 9 | 10 | Mean |
| a | 3 | 3 | 3 | 3 | 3 | 3 | 3 | 3 | 3 | 3 | 3 |
| b | 3 | 3 | 3 | 3 | 3 | 3 | 3 | 3 | 3 | 3 | 3 |
| c | 3 | 3 | 3 | 3 | 3 | 3 | 3 | 3 | 3 | 3 | 3 |
| d | 3 | 3 | 3 | 3 | 3 | 3 | 3 | 3 | 3 | 3 | 3 |
| e | 3 | 3 | 3 | 3 | 3 | 3 | 3 | 3 | 3 | 3 | 3 |
| f | 3 | 3 | 3 | 3 | 3 | 3 | 3 | 3 | 3 | 3 | 3 |
| g | 3 | 3 | 3 | 3 | 3 | 3 | 3 | 3 | 3 | 3 | 3 |
| h | 3 | 3 | 3 | 3 | 3 | 3 | 3 | 3 | 3 | 3 | 3 |
| i | 3 | 3 | 3 | 3 | 3 | 3 | 3 | 3 | 3 | 3 | 3 |
| j | 3 | 3 | 3 | 3 | 3 | 3 | 3 | 3 | 3 | 3 | 3 |
| k | 3 | 3 | 3 | 3 | 3 | 3 | 3 | 3 | 3 | 3 | 3 |

TABLE 11

| Type of base in drug-containing layer | Test subject | | | | | | | | | | |
|---|---|---|---|---|---|---|---|---|---|---|---|
| | 1 | 2 | 3 | 4 | 5 | 6 | 7 | 8 | 9 | 10 | Mean |
| a | 3 | 3 | 3 | 3 | 3 | 3 | 3 | 3 | 3 | 3 | 3 |
| b | 3 | 3 | 3 | 3 | 3 | 3 | 3 | 3 | 3 | 3 | 3 |
| c | 3 | 3 | 3 | 3 | 3 | 3 | 3 | 3 | 3 | 3 | 3 |
| d | 3 | 3 | 3 | 3 | 3 | 3 | 3 | 3 | 3 | 3 | 3 |
| e | 3 | 3 | 3 | 3 | 3 | 3 | 3 | 3 | 3 | 3 | 3 |
| f | 3 | 3 | 3 | 3 | 3 | 3 | 3 | 3 | 3 | 3 | 3 |
| g | 3 | 3 | 3 | 3 | 3 | 3 | 3 | 3 | 3 | 3 | 3 |
| h | 3 | 3 | 3 | 3 | 3 | 3 | 3 | 3 | 3 | 3 | 3 |
| i | 3 | 3 | 3 | 3 | 3 | 3 | 3 | 3 | 3 | 3 | 3 |
| j | 3 | 3 | 3 | 3 | 3 | 3 | 3 | 3 | 3 | 3 | 3 |
| k | 3 | 3 | 3 | 3 | 3 | 3 | 3 | 3 | 3 | 3 | 3 |

As shown in Tables 10 and 11, the flavor of the drug contained in the drug-containing layer was completely masked regardless of the type of base contained in the drug-containing layer whether the outer edges of the water-swellable gel-forming layers were bonded directly to each other (orally administered pharmaceutical composition A) or were bonded to each other via adhesive layers (orally administered pharmaceutical composition B).

Test Example 6

The ability to mask the flavor of the drug was evaluated as in Test Example 5 with respect to the orally administered pharmaceutical compositions C through F produced in Production Example 4. The results are shown in Table 12.

TABLE 12

| Type of orally administered pharmaceutical composition | Test subject | | | | | | | | | | Mean |
|---|---|---|---|---|---|---|---|---|---|---|---|
| | 1 | 2 | 3 | 4 | 5 | 6 | 7 | 8 | 9 | 10 | |
| C | 3 | 3 | 3 | 3 | 3 | 3 | 3 | 3 | 3 | 3 | 3 |
| D | 3 | 3 | 3 | 3 | 3 | 3 | 3 | 3 | 3 | 3 | 3 |
| E | 3 | 3 | 3 | 2 | 3 | 3 | 3 | 3 | 3 | 3 | 2.9 |
| F | 3 | 3 | 3 | 3 | 3 | 2 | 3 | 2 | 3 | 3 | 2.8 |

As shown in Table 12, the flavor of the drug contained in the drug-containing layer was entirely masked regardless of the form of the drug enclosed inside the orally administered pharmaceutical composition.

INDUSTRIAL APPLICABILITY

According to the present invention, an orally administered agent according to which the ease and safety of taking the agent are improved, a film-shaped orally administered agent that can contain a broad range of types of drugs, and an orally administered agent according to which a drop in compliance of taking a drug due to the taste (e.g. bitterness, astringency) or smell of the drug can be prevented, are provided. Moreover, according to the present invention, an orally administered agent/supporting substrate complex according to which handling of an orally administered agent (e.g. carrying, storage etc. of the orally administered agent) can be made easy, an orally administered agent/supporting substrate complex according to which an orally administered agent can be administered easily, and an orally administered agent/supporting substrate complex according to which it can easily be checked whether or not an orally administered agent has been taken, are provided.

Also, according to one embodiment of the present invention, an orally administered pharmaceutical composition capable of completely masking the flavor, odor and the like of a drug contained in a drug-containing layer is provided.

The invention claimed is:

1. An orally administered agent comprising a drug-containing layer that contains a drug, a first water-swellable gel-forming layer that is provided on one side of said drug-containing layer, and a second water-swellable gel-forming layer that is provided on the other side of said drug-containing layer,
    wherein the first and second water-swellable gel-forming layers are formed from a composition that contains at least a water-swellable gel-forming agent of carboxyvinyl polymer, a film-forming agent, and a polyvalent metal compound as a cross-linking agent,
    the content of said water-swellable gel-forming agent in said composition is 13.5 to 70 wt %, and the content of said polyvalent metal compound in said composition is 1.5 to 5.6 wt %,
    said polyvalent metal compound is at least one of calcium chloride, magnesium chloride, aluminum chloride, aluminum sulfate, aluminum potassium sulfate, iron chloride alum, ammonium alum, ferric sulfate, aluminum hydroxide, aluminum silicate, aluminum phosphate, iron citrate, magnesium oxide, calcium oxide, zinc oxide and zinc sulfate,
    said first and second water-swellable gel-forming layers are provided over the whole of the faces of said drug-containing layer, outer edges of said first and second water-swellable gel-forming layers each having an adhesive layer thereon, and said adhesive layers of the outer edges of said first and second water-swellable gel-forming layers being bonded together so as to enclose said drug-containing layer inside the orally administered agent, and
    said drug is released in a stomach or an intestine from the orally administered agent after administration.

2. The orally administered agent according to claim 1, wherein said orally administered agent is a film-shaped preparation.

3. The orally administered agent according to claim 1, wherein said film-forming agent is at least one of a polyvinyl alcohol, polyvinyl pyrrolidone, hydroxyalkyl cellulose, and alkyl celluloses.

4. The orally administered agent according to claim 1, wherein said first and second water-swellable gel-forming layers do not contain a drug.

5. The orally administered agent according to claim 1, wherein said first and second water-swellable gel-forming layers are provided as an outermost layer of the orally administered agent.

6. A method of an administration of a drug using an orally administered agent comprising a drug-containing layer that contains a drug, a first water-swellable gel-forming layer that is provided on one side of said drug-containing layer, and a second water-swellable gel-forming layer that is provided on the other side of said drug-containing layer, comprising
    a step of inserting said orally administered agent into a mouth without water,
    a step of swelling said water-swellable gel-forming layer by a saliva in the mouth,
    a step of swallowing the swelled orally administered agent, and
    a step of releasing the drug in a stomach or an intestine,
    wherein said first and second water-swellable gel-forming layers are formed from a composition containing at least a water-swellable gel-forming agent of carboxyvinyl polymer, a film-forming agent and a polyvalent metal compound as a cross-linking agent,
    the content of said water-swellable gel-forming agent in said composition is 13.5 to 70 wt %, and the content of the polyvalent metal compound in said composition is 1.5 to 5.6 wt %,
    said polyvalent metal compound is at least one of calcium chloride, magnesium chloride, aluminum chloride, aluminum sulfate, aluminum potassium sulfate, iron chloride alum, ammonium alum, ferric sulfate, aluminum hydroxide, aluminum silicate, aluminum phosphate, iron citrate, magnesium oxide, calcium oxide, zinc oxide and zinc sulfate, and
    said first and second water-swellable gel-forming layers are provided over the whole of the faces of said drug-containing layer, and
    the outer edge of the first water-swellable gel forming layer and the outer edge of the second water-swellable gel-forming layer are bonded together by heat fusion via an adhesive layer containing a heat-fusable adhesive so as to enclose said drug-containing layer inside the orally administered agent.

7. The method of the administration of a drug according to 6, wherein said film-forming agent is at least of one of a polyvinyl alcohol, polyvinyl pyrrolidone, hydroxyalkyl cellulose and alkyl celluloses.

8. The method of the administration of a drug according to claim 6, wherein said first and second water-swellable gel-forming layers do not contain a drug.

9. The method of the administration of a drug according to claim 6, wherein said orally administered agent is a film-shaped preparation.

10. The method of the administration of a drug according to claim 6, wherein said first and second water-swellable gel-forming layers are provided as an outermost layer of the orally administered agent.

11. An orally administered agent/supporting substrate complex comprising a drug-containing layer that contains drug, an orally administered agent that contains water-swellable gel-forming layers, and a supporting substrate that supports the orally administered agent,
wherein said orally administered agent is provided on said supporting substrate either directly or via an intermediate layer,
said water-swellable gel-forming layers are formed from a composition containing at least a water-swellable gel-forming agent of carboxyvinyl polymer, a film-forming agent and a polyvalent metal compound as a cross-linking agent, the outer edge of a first water-swellable gel forming layer and the outer edge of a second water-swellable gel-forming layer are bonded together by heat fusion via an adhesive layer containing a heat-fusable adhesive so as to enclose said drug-containing layer inside the orally administered agent,
the content of said water-swellable gel-forming agent in said composition is 13.5 to 70 wt %, and the content of the polyvalent metal compound in said composition is 1.5 to 5.6 wt %,
said polyvalent metal compound is at least one of calcium chloride, magnesium chloride, aluminum chloride, aluminum sulfate, aluminum potassium sulfate, iron chloride alum, ammonium alum, ferric sulfate, aluminum hydroxide, aluminum silicate, aluminum phosphate, iron citrate, magnesium oxide, calcium oxide, zinc oxide and zinc sulfate,
said supporting substrate is composed of a soluble material that dissolves in a mouth, and
said supporting substrate has a gripping part and a mouth-inserting part, and said orally administered agent is provided on said mouth-inserting part.

12. An orally administered agent comprising a drug-containing layer that contains a drug, a first water-swellable gel-forming layer that is provided on one side of said drug-containing layer, and a second water-swellable gel-forming layer that is provided on the other side of said drug-containing layer,
wherein the outer edge of the first water-swellable gel forming layer and the outer edge of the second water-swellable gel-forming layer are bonded together by heat fusion via an adhesive layer containing a heat-fusable adhesive so as to enclose said drug-containing layer inside the orally administered pharmaceutical composition,
said first and second water-swellable gel-forming layers are formed from a composition containing at least a water-swellable gel-forming agent of carboxyvinyl polymer, a film-forming agent and a polyvalent metal compound as a cross-linking agent,
the content of said water-swellable gel-forming agent in said composition is 13.5 to 70 wt %, and the content of the polyvalent metal compound in said composition is 1.5 to 5.6 wt %,
said polyvalent metal compound is at least one of calcium chloride, magnesium chloride, aluminum chloride, aluminum sulfate, aluminum potassium sulfate, iron chloride alum, ammonium alum, ferric sulfate, aluminum hydroxide, aluminum silicate, aluminum phosphate, iron citrate, magnesium oxide, calcium oxide, zinc oxide and zinc sulfate, and
said drug is released in a stomach or an intestine from the orally administered agent after administration.

13. The orally administered agent according to claim 12, wherein said film-forming agent is at least one of a polyvinyl alcohol, polyvinyl pyrrolidone, hydroxyalkyl cellulose and alkyl celluloses.

14. The orally administered agent according to claim 12, wherein said drug-containing layer comprises a molded tablet, and the outer edge of the first water-swellable gel forming layer and the outer edge of the second water-swellable gel-forming layer are bonded together so as to enclose the molded tablet inside the orally administered pharmaceutical composition.

15. The orally administered agent according to claim 14, wherein said film-forming agent is at least one of polyvinyl alcohol, polyvinyl pyrrolidone, hydroxyalkyl cellulose and alkyl celluloses.

* * * * *